United States Patent
Jennewein et al.

(10) Patent No.: US 11,066,685 B2
(45) Date of Patent: Jul. 20, 2021

(54) FERMENTATION PROCESS FOR PRODUCING MONOSACCHARIDES IN FREE FORM FROM NUCLEOTIDE-ACTIVATED SUGARS

(71) Applicant: JENNEWEIN BIOTECHNOLOGIE GMBH, Rheinbreitbach (DE)

(72) Inventors: Stefan Jennewein, Bad Honnef (DE); Katja Parschat, Bonn (DE)

(73) Assignee: Jennewein Biotechnologie GmbH, Rheinbreitbach (DE)

( * ) Notice: Subject to any disclaimer, the term of this patent is extended or adjusted under 35 U.S.C. 154(b) by 0 days.

(21) Appl. No.: 15/546,778

(22) PCT Filed: Jan. 29, 2016

(86) PCT No.: PCT/EP2016/051919
§ 371 (c)(1),
(2) Date: Jul. 27, 2017

(87) PCT Pub. No.: WO2016/120448
PCT Pub. Date: Aug. 4, 2016

(65) Prior Publication Data
US 2018/0273996 A1    Sep. 27, 2018

(30) Foreign Application Priority Data
Jan. 30, 2015  (EP) .................... 15153383

(51) Int. Cl.
C12P 19/18 (2006.01)
C12P 19/02 (2006.01)
C12N 9/10 (2006.01)

(52) U.S. Cl.
CPC ............ *C12P 19/02* (2013.01); *C12N 9/1051* (2013.01); *C12P 19/18* (2013.01)

(58) Field of Classification Search
None
See application file for complete search history.

(56) References Cited

U.S. PATENT DOCUMENTS

2014/0031541 A1    1/2014  Heidtman et al.

FOREIGN PATENT DOCUMENTS

| EP | 1243647 A1 | 9/2002 |
| EP | 2479263 A1 | 7/2012 |
| WO | 2010/036898 A1 | 4/2010 |
| WO | 2014/067696 A1 | 5/2014 |

OTHER PUBLICATIONS

Li et al. (Energy & Fuels, 2008, vol. 22, pp. 2015-2021).*
Stein, Daniel B. et al., "Characterization of Helicobacter pylori [alpha]1,2-Fucosyltransferase for Enzymatic Synthesis of Tumor-Associated Antigens", Advanced Synthesis & Catalysis, Oct. 6, 2008, pp. 2313-2321, vol. 350, No. 14-15.
De Vries, Theodora et al., "Acceptor Specificity of Different Length Constructs of Human Recombinant [alpha]1,3/4-Fucosyltransferases: Replacement of the Stem Region and the Transmembrane Domain of Fucosytransferase V By Protein A Results in an Enzyme With GDP-Fucose Hydrolyzing Activity", Journal of Biological Chemistry, Apr. 14, 1995, pp. 8712-8722, vol. 270, No. 15.
Legler, Patricia M. et al., "GDP-Mannose Mannosyl Hydrolase Catalyzes Nucleophilic Substitution at Carbon Unlike All Other Nudix Hydrolases", Biochemistry, Jul. 1, 2000, pp. 8603-8608, vol. 39, No. 29.
Baumgaertner, Florian et al., "Construction of *Escherichia coli* strains with chromosomally integrated expression cassettes for the synthesis of 2'-fucosyllactose", Microbial Cell Factories, May 1, 2013, pp. 1-13, vol. 12, No. 1, 40, Biomed Central, London, GB.
International Search Report of International Patent Application No. PCT/EP2016/051919 dated Jun. 27, 2016.
Engels, Leonie, and Lothar Elling. "WbgL: a novel bacterial α1,2-fucosyltransferase for the synthesis of 2'-fucosyllactose." Glycobiology, (2014), vol. 24, No. 2: 170-178.

* cited by examiner

*Primary Examiner* — Hope A Robinson
(74) *Attorney, Agent, or Firm* — McBee Moore & Vanik IP, LLC

(57) ABSTRACT

The present invention relates to a process for producing a monosaccharide, e.g. L-fucose, in free form using a microbial fermentation process. The used microorganism exhibits hydrolase activity on nucleotide-activated sugars and releases the monosaccharide in an unmodified free form. The free monosaccharide is retrieved from the supernatant of the cultivated microorganism.

Figure 1:
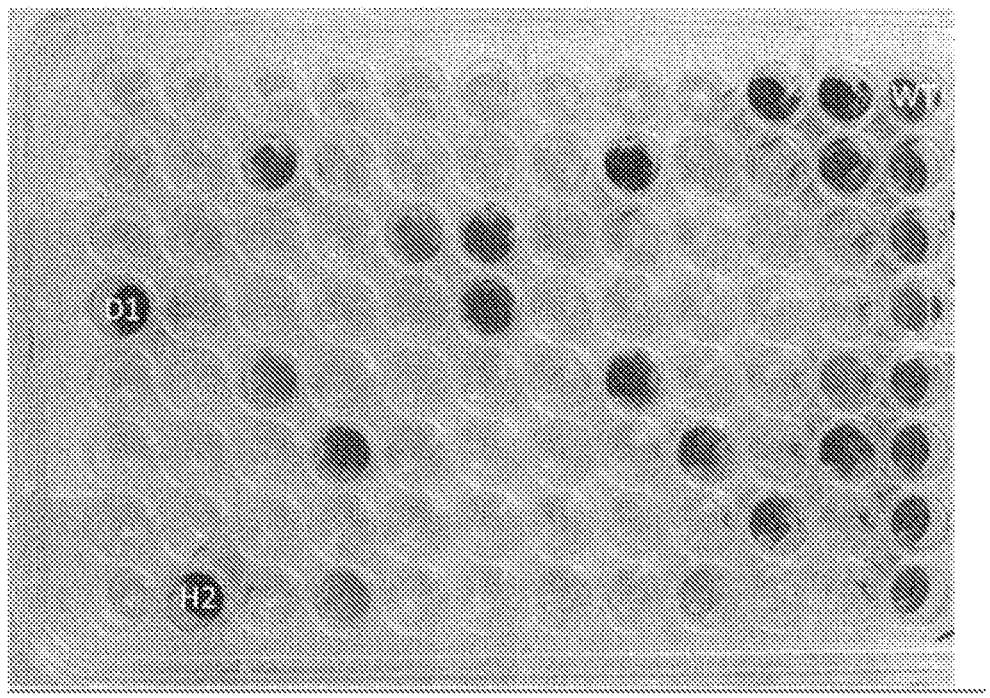

12 Claims, 10 Drawing Sheets
Specification includes a Sequence Listing.

Fig. 4A

SEQ ID NO. 1: <P$_{tuf}$-manCB-P$_{tS}$-gmd, wcaG- dhfr >

GGCCAGATGATTAATTCCTAATTTTTGTTGACACTCTATCATTGATAGAGTTATTTTACCACTCCCTA
TCAGTGATAGAGAAAAGTGAAATGAATAGTTCGACAAAAATCTAGAAATAATTTTGTTTAACTTTAAG
AAGGAGATATACAATTTCGTCGACACACAGGAAACATATTAAAAATTAAAACCTGCAGGAGTTTGAAG
GAGATAGAACCATGGCGCAGTCGAAACTCTATCCAGTTGTGATGGCAGGTGGCTCCGGTAGCCGCTTA
TGGCCGCTTTCCCGCGTACTTTATCCCAAGCAGTTTTATGCCTGAAAGGCGATCTCACCATGCTGCA
AACCACCATCTGCCGCCTGAACGGCGTGGAGTGCGAAAGCCCGGTGGTGATTTGCAATGAGCAGCACC
GCTTTATTGTCGCGGAACAGCTGCGTCAACTGAACAAACTTACCGAGAACATTATTCTCGAACCGGCA
GGGCGAAACACGGCACCTGCCATTGCGCTGGCGGCGCTGGCGGCAAAACGTCATAGCCCGGAGAGCGA
CCCGTTAATGCTGGTATTGGCGGCGGATCATGTGATTGCCGATGAAGACGCGTTCCGTGCCGCCGTGC
GTAATGCCATGCCATATGCCGAAGCGGGCAAGCTGGTGACCTTCGGCATTGTGCCGGATCTACCAGAA
ACCGGTTATGGCTATATTCGTCGCGGTGAAGTGTCTGCGGGTGAGCAGGATATGGTGGCCTTTGAAGT
GGCGCAGTTTGTCGAAAAACCGAATCTGGAAACCGCTCAGGCCTATGTGGCAAGCGGCGAATATTACT
GGAACAGCGGTATGTTCCTGTTCCGCGCCGGACGCTATCTCGAAGAACTGAAAAAATATCGCCCGGAT
ATCCTCGATGCCTGTGAAAAGCGATGAGCGCCGTCGATCCGGATCTCAATTTTATTCGCGTGGATGA
AGAAGCGTTTCTCGCCTGCCCCGGAAGAGTCGGTGGATTACGCGGTCATGGAACGTACGGCAGATGCTG
TTGTGGTGCCGATGGATGCGGGCTGGAGCGATGTTGGCTCCTGGTCTTCATTATGGGAGATCAGCGCC
CACACCGCCGAGGGCAACGTTTGCCACGGCGATGTGATTAATCACAAAACTGAAAACAGCTATGTGTA
TGCTGAATCTGGCCTGGTCACCACCGTCGGGGTGAAAGATCTGGTAGTGGTGCAGACCAAAGATGCGG
TGCTGATTGCCGACCGTAACGCGGTACAGGATGTGAAAAAAGTGGTCGAGCAGATCAAAGCCGATGGT
CGCCATGAGCATCGGGTGCATCGCGAAGTGTATCGTCCGTGGGCAAATATGACTCTATCGACGCGGG
CGACCGCTACCAGGTGAAACGCATCACCGTGAAACCGGGCGAGGGCTTGTCGGTACAGATGCACCATC
ACCGCGCGGAACACTGGGTGGTTGTCGCGGGAACGGCAAAAGTCACCATTGATGGTGATATCAAACTG
CTTGGTGAAAACGAGTCCATTTATATTCCGCTGGGGGCGACGCATTGCCTGGAAAACCCGGGGAAAAT
TCCGCTCGATTTAATTGAAGTGCGCTCCGGCTCTTATCTCGAAGAGGATGATGTGGTGCGTTTCGCGG
ATCGCTACGGACGGGTGTAAACGTCGCATCAGGCAATGAATGCGAAACCGCGGTGTAAATAACGACAA
AAATAAAATTGGCCGCTTCGGTCAGGCCAACTATTGCCTGAAAAAGGGTAACGATATGAAAAATTA
ACCTGCTTTAAAGCCTATGATATTCGCGGGAAATTAGGCGAAGAACTGAATGAAGATATCGCCTGGCG
CATTGGTCGCGCCTATGGCGAATTTCTCAAACCGAAAACCATTGTGTTAGGCGGTGATGTCCGCCTCA
CCAGCGAAACCTTAAAACTGGCGCTGGCGAAAGGTTTACAGGATGCGGGCGTTGACGTGCTGGATATT
GGTATGTCCGGCACCGAAGAGATCTATTTCGCCACGTTCCATCTCGGCGTGGATGGCGGCATTGAAGT
TACCGCCAGCCATAATCCGATGGATTATAACGGCATGAAGCTGGTTCGCGAGGGGGCTCGCCCCGATCA
GCGGAGATACCGGACTGCGCGACGTCCAGCGTCTGGCTGAAGCCAACGACTTTCCTCCCGTCGATGAA

Fig. 4A (Continued)

```
ACCAAACGCGGTCGCTATCAGCAAATCAACCTGCGTGACGCTTACGTTGATCACCTGTTCGGTTATAT
CAATGTCAAAAACCTCACGCCGCTCAAGCTGGTGATCAACTCCGGGAACGGCGCAGCGGGTCCGGTGG
TGGACGCCATTGAAGCCCGCTTTAAAGCCCTCGGCGCGCCCGTGGAATTAATCAAAGTGCACAACACG
CCGGACGGCAATTTCCCCAACGGTATTCCTAACCCACTACTGCCGGAATGCCGCGACGACACCCGCAA
TGCGGTCATCAAACACGGCGCGGATATGGGCATTGCTTTTGATGGCGATTTTGACCGCTGTTTCCTGT
TTGACGAAAAAGGGCAGTTTATTGAGGGCTACTACATTGTCGGCCTGTTGGCAGAAGCATTCCTCGAA
AAAAATCCCGGCGCGAAGATCATCCACGATCCACGTCTCTCCTGGAACACCGTTGATGTGGTGACTGC
CGCAGGTGGCACGCCGGTAATGTCGAAAACCGGACACGCCTTTATTAAAGAACGTATGCGCAAGGAAG
ACGCCATCTATGGTGGCGAAATGAGCGCCCACCATTACTTCCGTGATTTCGCTTACTGCGACAGCGGC
ATGATCCCCGTGGCTGCTGGTCGCCGAACTGGTGTGCCTGAAAGATAAAACGCTGGGCGAACTGGTACG
CGACCGGATGGCGGCGTTTCCGGCAAGCGGTGAGATCAACAGCAAACTGGCGCAACCCGTTGAGGCGA
TTAACCGCGTGGAACAGCATTTTAGCCGTGAGGCGCTGGCGGTGGATCGCACCGATGGCATCAGCATG
ACCTTTGCCGACTGGCGCTTTAACCTGCGCACCTCCAATACCGAACCGGTGGTGCGCCTGAATGTGGA
ATCGCGCGGTGATGTGCCCGCTGATGGAAGCGCGAACGCGAACTCTGCTGACGTTGCTGAACGAGTAAA
AACGCGGCCGCGATATCGTTGTAAAACGACGGCCAGTGCAAGAATCATAAAAAATTTATTTGCTTTCA
GGAAAATTTTTCTGTATAATAGATTCATAAATTTGAGAGAGGAGTTTTTGTGAGCGGATAACAATTCC
CCATCTTAGTATATTAGTTAAGTATAAATACACCGCGGAGGACGAAGGAGATAGAACCATGTCAAAAG
TCGCTCTCATCACCGGTGTAACCGGACAAGACGGTTCTTACCTGGCAGAGTTTCTGCTGGAAAAAGGT
TACGAGGTGCATGGTATTAAGCGTCGCGCATCGTCATTCAACACCGAGCGCGTGGATCACATTTATCA
GGATCCGCACACCTGCAACCCGAAATTCCATCTGCATTATGGCGACCTGAGTGATACCTCTAACCTGA
CGCGCATTTTGCGTGAAGTACAGCCGGATGAAGTGTACAACCTGGGCGCAATGAGCCACGTTGCGGTC
TCTTTTGAGTCACCAGAATATACCGCTGACGTCGACGCGATGGGTACGCTGCGCCTGCTGGAGGCGAT
CCGCTTCCTCGGTCTGGAAAAGAAAACTCGTTTCTATCAGGCTTCCACCTCTGAACTGTATGGTCTGG
TGCAGGAAATTCCGCAGAAGAGACCACGCCGTTCTACCCGCGATCTCCGTATGCGGTCGCCAAACTG
TACGCCTACTGGATCACCGTTAACTACCGTGAATCCTACGGCATGTACGCCTGTAACGGAATTCTCTT
CAACCATGAATCCCCGCGCCGCGGCGAAACCTTCGTTACCCGCAAAATCACCCGCGCAATCGCCAACA
TCGCCCAGGGGCTGGAGTCGTGCCTGTACCTCGGCAATATGGATTCCCTGCGTGACTGGGGCCACGCC
AAAGACTACGTAAAAATGCAGTGGATGATGCTGCAGCAGGAACAGCCGGAAGATTTCGTTATCGCGAC
CGGCGTTCAGTACTCCGTGCGTCAGTTCGTGGAAATGGCGGCAGCACAGCTGGGCATCAAACTGCGCT
TTGAAGGCACGGGCGTTGAAGAGAAGGGCATTGTGGTTTCCGTCACCGGGCATGACGCGCCGGGCGTT
AAACCGGGTGATGTGATTATCGCTGTTGACCCGCGTTACTTCCGTCCGGCTGAAGTTGAAACGCTGCT
CGGCGACCCGACCAAAGCGCACGAAAAACTGGGCTGGAAACCGGAAATCACCCTCAGAGAGATGGTGT
CTGAAATGGTGGCTAATGACCTCGAAGCGGCGAAAAAACACTCTCTGCTGAAATCTCACGGCTACGAC
GTGGCGATCGCGCTGGAGTCATAAGCATGAGTAAACAACGAGTTTTTATTGCTGGTCATCGCGGGATG
```

Fig. 4A (Continued)

```
GTCGGTTCCGCCATCAGGCGGCAGCTCGAACAGCGCGGTGATGTGGAACTGGTATTACGCACCCGCGA
CGAGCTGAACCTGCTGGACAGCCGCGCCGTGCATGATTTCTTTGCCAGCGAACGTATTGACCAGGTCT
ATCTGGCGGCGGCGAAAGTGGGCGGCATTGTTGCCAACAACACCTATCCGGCGGATTTCATCTACCAG
AACATGATGATTGAGAGCAACATCATTCACGCCGCGCATCAGAACGACGTGAACAAACTGCTGTTTCT
CGGATCGTCCTGCATCTACCCGAAACTGGCAAAACAGCCGATGGCAGAAAGCGAGTTGTTGCAGGGCA
CGCTGGAGCCGACTAACGAGCCTTATGCTATTGCCAAAATCGCCGGGATCAAACTGTGCGAATCATAC
AACCGCCAGTACGGACGCGATTACCGCTCAGTCATGCCGACCAACCTGTACGGGCCACACGACAACTT
CCACCCGAGTAATTCGCATGTGATCCCAGCATTGCTGCGTCGCTTCCACGAGGCGACGGCACAGAATG
CGCCGGACGTGGTGGTATGGGGCAGCGGTACACCGATGCGCGAATTTCTGCACGTCGATGATATGGCG
GCGGCGAGCATTCATGTCATGGAGCTGGCGCATGAAGTCTGGCTGGAGAACACCCAGCCGATGTTGTC
GCACATTAACGTCGGCACGGGCGTTGACTGCACTATCCGCGAGCTGGCGCAAACCATCGCCAAAGTGG
TGGGTTACAAAGGCCGGGTGGTTTTTGATGCCAGCAAACCGGATGGCACGCCGCGCAAACTGCTGGAT
GTGACGCGCCTGCATCAGCTTGGCTGGTATCACGAAATCTCACTGGAAGCGGGGCTTGCCAGCACTTA
CCAGTGGTTCCTTGAGAATCAAGACCGCTTTCGGGGGGGAGCTAACGCGCCATTTAAATCAACCTCA
GCGGTCATAGCTGTTTCCTGTGACTGAGCAATAACTAGCATAACCCCTTGGGGCCTCTAAACGGGTCT
TGAGGGGTTTTTTGCTGAAACCAATTTGCCTGCCGGCAGTAGCGCGGTGGTCCCACCTGACCCCATGC
CGAACTCAGAAGTGAAACGCCGTAGCGCCGATGGTAGTGTGGGGTCTCCCCATGCGACAGTAGGGAAC
TGCCAGGCATCAAATAAAACGAAAGGCTCAGTCGAAAGACTGGGCCTTTCGGGATCCAGGCCGGCCTG
TTAACGAATTAATCTTCCGCGGCGGTATCGATAAGCTTGATATCGAATTCCGAAGTTCCTATTCTCTA
GAAAGTATAGGAACTTCAGGTCTGAAGAGGAGTTTACGTCCAGCCAAGCTAGCTTGGCTGCAGGTCGT
CGAAATTCTACCGGGTAGGGGAGGCGCTTTTCCCAAGGCAGTCTGGAGCATGCGCTTTAGCAGCCCCG
CTGGGCACTTGGCGCTACACAAGTGGCCTCTGGCCTCGCACACATTCCACATCCACCGGTAGGCGCCA
ACCGGCTCCGTTCTTTGGTGGCCCCTTCGCGCCACCTTCTACTCCTCCCCTAGTCAGGAAGTTCCCCC
CCGCCCCGCAGCTCGCGTCGTGCAGGACGTGACAAATGGAAGTAGCACGTCTCACTAGTCTCGTGCAG
ATGGACAGCACCGCTGAGCAATGGAAGCGGGTAGGCCTTTGGGGCAGCGGCCAATAGCAGCTTTGCTC
CTTCGCTTTCTGGGCTCAGAGGCTGGGAAGGGGTGGGTCCGGGGCGGGCTCAGGGGCGGGCTCAGGG
GCGGGGCGGGCGCCCGAAGGTCCTCCGGAGGCCCGGCATTCTGCACGCTTCAAAAGCGCACGTCTGCC
GCGCTGTTCTCCTCTTCCTCATCTCCGGCCTTTCGACCTGCAGCCTGTTGACAATTAATCATCGGCA
TAGTATATCGGCATAGTATAATACGACAAGGTGAGGAACTAAACCATGGGTCAAAGTAGCGATGAAGC
CAACGCTCCCGTTGCAGGGCAGTTTGCGCTTCCCCTGAGTGCCACCTTTGGCTTAGGGGATCGCGTAC
GCAAGAAATCTGGTGCCGCTTGGCAGGGTCAAGTCGTCGGTTGGTATTGCACAAAACTCACTCCTGAA
GGCTATGCGGTCGAGTCCGAATCCCACCCAGGCTCAGTGCAAATTTATCCTGTGGCTGCACTTGAACG
TGTGGCCTAATGAGGGGATCAATTCTCTAGAGCTCGCTGATCAGAAGTTCCTATTCTCTAGAAAGTAT
AGGAACTTC
```

Fig. 4B SEQ ID No. 2: <cscB-cscK-cscA-cscR>

GCGACTGTACCAGAACATGAATGAGGCGTTTGGATTAGGCGATTATTAGCAGGGCTAAGCATTTTACT
ATTATTATTTTCCGGTTGAGGGATATAGAGCTATCGACAACAACCGGAAAAAGTTTACGTCTATATTG
CTGAAGGTACAGGCGTTTCCATAACTATTTGCTCGCGTTTTTTACTCAAGAAGAAAATGCCAAATAGC
AACATCAGGCAGACAATACCCGAAATTGCGAAGAAAACTGTCTGGTAGCCTGCGTGGTCAAAGAGTAT
CCCAGTCGGCGTTGAAAGCAGCACAATCCCAAGCGAACTGGCAATTTGAAAACCAATCAGAAAGATCG
TCGACGACAGGCGCTTATCAAAGTTTGCCACGCTGTATTTGAAGACGGATATGACACAAAGTGGAACC
TCAATGGCATGTAACAACTTCACTAATGAAATAATCCAGGGGTTAACGAACAGCGCGCAGGAAAGGAT
ACGCAACGCCATAATCACAACTCCGATAAGTAATGCATTTTTTGGCCCTACCCGATTCACAAAGAAAG
GAATAATCGCCATGCACAGCGCTTCGAGTACCACCTGGAATGAGTTGAGATAACCATACAGGCGCGTT
CCTACATCGTGTGATTCGAATAAACCTGAATAAAAGACAGGAAAAAGTTGTTGATCAAAAATGTTATA
GAAAGACCACGTCCCCACAATAAATATGACGAAAACCCAGAAGTTTCGATCCTTGAAAACTGCGATAA
AATCCTCTTTTTTACCCCTCCCGCATCTGCCGCTACGCACTGGTGATCCTTATCTTTAAAACGCATG
TTGATCATCATAAATACAGCGCCAAATAGCGAGACCAACCAGAAGTTGATATGGGGACTGATACTAAA
AAATATGCCGGCAAAGAACGCGCCAATAGCATAGCCAAAAGATCCCCAGGCGCGCGCTGTTCCATATT
CGAAATGAAAATTTCGCGCCATTTTTTCGGTGAAGCTATCAAGCAAACCGCATCCCGCCAGATACCCC
AAGCCAAAAAATAGCGCCCCAGAATTAGACCTACAGAAAAATTGCTTTGCAGTAACGGTTCATAAAC
GTAAATCATAAACGGTCCGGTCAAGACCAGGATGAAACTCATACACCAGATGAGCGGTTTCTTCAGAC
CGAGTTTATCCTGAACGATGCCGTAGAACATCATAAATAGAATGCTGGTAAACTGGTTGACCGAATAA
AGTGTACCTAATTCCGTCCCTGTCAACCCTAGATGTCCTTTCAGCCAAATAGCGTATAACGACCACCA
CAGCGACCAGGAAATAAAAAGAGAAATGAGTAACTGGATGCAAAACGATAGTACGCATTTCTGAATG
GAATATTCAGTGCCATAATTACCTGCCTGTCGTTAAAAAATTCACGTCCTATTTAGAGATAAGAGCGA
CTTCGCCGTTTACTTCTCACTATTCCAGTTCTTGTCGACATGGCAGCGCTGTCATTGCCCCTTTCGCC
GTTACTGCAAGCGCTCCGCAACGTTGAGCGAGATCGATAATTCGTCGCATTTCTCTCTCATCTGTAGA
TAATCCCGTAGAGGACAGACCTGTGAGTAACCCGGCAACGAACGCATCTCCCGCCCCCGTGCTATCGA
CACAATTCACAGACATTCCAGCAAAATGGTGAACTTGTCCTCGATAACAGACCACCACCCCTTCTGCA
CCTTTAGTCACCAACAGCATGGCGATCTCATACTCTTTGCCAGGGCGCATATATCCTGATCGTTCTG
TGTTTTTCCACTGATAAGTCGCCATTCTTCTTCCGAGAGCTTGACGACATCCGCCAGTTGTAGCGCCT
GCCGCAAACACAAGCGGAGCAAATGCTCGTCTTGCCATAGATCTTCACGAATATTAGGATCGAAGCTG
ACAAAACCTCCGGCATGCCGGATCGCCGTCATCGCAGTAAATGCGCTGGTACGCGAAGGCTCGGCAGA
CAACGCAATTGAACAGAGATGTAACCATTCGCCATGTCGCCAGCAGGGCAAGTCTGTCGTCTCTAAAA
AAAGATCGGCACTGGGGCGGACCATAAACGTAAATGAACGTTCCCCTTGATCGTTCAGATCGACAAGC
ACCGTGGATGTCCGGTGCCATTCATCTTGCTTCAGATACGTGATATCGACTCCCTCAGTTAGCAGCGT
TCTTTGCATTAACGCACCAAAAGGATCATCCCCCACCCGACCTATAAACCCACTTGTTCCGCCTAATC
TGGCGATTCCCACCGCAACGTTAGCTGGCGCGCCGCCAGGACAAGGCAGTAGGCGCCCGTCTGATTCT

Fig. 4B (Continued)

```
GGCAAGAGATCTACGACCGCATCCCCTAAAACCCATACTTTGGCTGACATTTTTTCCCTTAAATTCA
TCTGAGTTACGCATAGTGATAAACCTCTTTTTCGCAAAATCGTCATGGATTTACTAAAACATGCATAT
TCGATCACAAAACGTCATAGTTAACGTTAACATTTGTGATATTCATCGCATTTATGAAAGTAAGGGAC
TTTATTTTTATAAAAGTTAACGTTAACAATTCACCAAATTTGCTTAACCAGGATGATTAAAATGACGC
AATCTCGATTGCATGCGGCGCAAAACGCCCTAGCAAAACTTCATGAGCACCGGGGTAACACTTTCTAT
CCCCATTTTCACCTCGCGCCTCCTGCCGGGTGGATGAACGATCCAAACGGCCTGATCTGGTTTAACGA
TCGTTATCACGCGTTTTATCAACATCATCCGATGAGCGAACACTGGGGGCCAATGCACTGGGGACATG
CCACCAGCGACGATATGATCCACTGGCAGCATGAGCCTATTGCGCTAGCGCCAGGAGACGATAATGAC
AAAGACGGGTGTTTTTCAGGTAGTGCTGTCGATGACAATGGTGTCCTCTCACTTATCTACACCGGACA
CGTCTGGCTCGATGGTGCAGGTAATGACGATGCAATTCGCGAAGTACAATGTCTGGCTACCAGTCGGG
ATGGTATTCATTTCGAGAAACAGGGTGTGATCCTCACTCCACCAGAAGGAATCATGCACTTCCGCGAT
CCTAAAGTGTGGCGTGAAGCCGACACATGGTGGATGGTAGTCGGGGCGAAAGATCCAGGCAACACGGG
GCAGATCCTGCTTTATCGCGGCAGTTCGTTGCGTGAATGGACCTTCGATCGCGTACTGGCCCACGCTG
ATGCGGGTGAAAGCTATATGTGGGAATGTCCGGACTTTTTCAGCCTTGGCGATCAGCATTATCTGATG
TTTTCCCCGCAGGGAATGAATGCCGAGGGATACAGTTACCGAAATCGCTTTCAAAGTGGCGTAATACC
CGGAATGTGGTCGCCAGGACGACTTTTTGCACAATCCGGGCATTTTACTGAACTTGATAACGGGCATG
ACTTTTATGCACCACAAAGCTTTTTAGCGAAGCATGGTCGGCGTATTGTTATCGGCTGGATGGATATG
TGGGAATCGCCAATGCCCTCAAAACGTGAAGGATGGGCAGGCTGCATGACGCTGGCGCGCGAGCTATC
AGAGAGCAATGGCAAACTTCTACAACGCCCGGTACACGAAGCTGAGTCGTTACGCCAGCAGCATCAAT
CTGTCTCTCCCCGCACAATCAGCAATAAATATGTTTTGCAGGAAAACGCGCAAGCAGTTGAGATTCAG
TTGCAGTGGGCGCTGAAGAACAGTGATGCCGAACATTACGGATTACAGCTCGGCACTGGAATGCGGCT
GTATATTGATAACCAATCTGAGCGACTTGTTTTGTGGCGGTATTACCCACACGAGAATTTAGACGGCT
ACCGTAGTATTCCCCTCCCGCAGCGTGACACGCTCGCCCTAAGGATATTTATCGATACATCATCCGTG
GAAGTATTTATTAACGACGGGGAAGCGGTGATGAGTAGTCGAATCTATCCGCAGCCAGAAGAACGGGA
ACTGTCGCTTTATGCCTCCCACGGAGTGGCTGTGCTGCAACATGGAGCACTCTGGCTACTGGGTTAAC
ATAATATCAGGTGGAACAACGGATCAACAGCGGCAAGGGATCCGCGTCACTCTTCCCCCTTCACGAC
CTTCAATAATATGCAATGCAGCTTCCCGCCCGATAATGTCATGTGGAAGCTGAATTGTGGTCAGCGGC
GGTAAAAACAGATGCCCGACGCCAACCAGATTATCAAAGCCCATTACGGCGACATCCTGCGGGATTCG
TACCCCCTTCGCCAGAAGAACCTGATAAGCCACAAAGGCTGCGCGATCGTTACCACATATCAGAACAT
CAAAATCTGGTTTGCCCGGTTTGAAGTGGGCATTGAGTAAACTTGCGAGATCGGTGTAGTGATCATCA
CCTGTTGCCATGTGAAATTGTTTCACCTCAGCCAGATCTCGTCCAGCATCACGCCAGGCCTGCTCAAA
TCCCTGCCGACGATACCCTGTTGCCAACGCACTTTCCGGTAGCCAGAAGCATAACGGTTGACGATAGC
CCGCCGCGAGCAAATGCTGTGTTGATTCATATTGTGCAGTGTAATCATCAGGGATATAACTGGGTAAC
GCTGGGTCATCCGCCACACAGTTCGCCAATACAATATTTTCACCATACAGAGACTCAGGCAGCGTGAT
```

Fig. 4B continued

ATGTCGCAGCCCATTGTAGTATAGATAATGCCATCCGGACGGTGGGCAAGCAGCTGACGTGCCGCG
GGGCAGCGTCATCTTCAGAAAAAATATTGATTAAAAAACTATTCCAGCCGAACTCGCTGGCGGTTTGC
TCAATGGCAAGCAGAATATCAACAGAGAAAGGAGTGGTAGCCGTGTCCTGCGCCAGCACGGCGAGAGT
CGACGGCTTACGTCCTTGAGCGCGCATCTTACGGGCGGAAAGATCAGGAACATAATTCAGGGTCTGGA
TTGCCTGCAATACGCGGTCACGCGTTGCAGGACGCACAGATTCTGCATTATGCATCACCCGGGAGACT
GTCATCATCGACACTCCCGCCAGGCGTGCGACATCCTTAATGAAGCCATACCCAAGCCGTTTGCCGT
AAAACGGGCACTGTAGCAGAAACAGACGTCACTGGCGAGATCCAACGCCCTATCACCTGACACAGCAA
TACAATAAAAAATAACAATAATTCCCGGACAATTGTCCCCAATTCCGCCTCTGTTCTCGC

Fig. 4C: SEQ ID No. 3: <wbgL>

ATGGGCAGCATTATTCGTCTGCAGGGTGGTCTGGGTAATCAGCTGTTTCAGTTTAGCTTTGGTTATGC
CCTGAGCAAAATTAATGGTACACCGCTGTATTTCGACATTAGCCATTATGCCGAAAACGATGATCATG
GTGGTTATCGTCTGAATAATCTGCAGATTCCGGAAGAATATCTGCAGTATTATACCCCGAAAATTAAT
AATATTTATAAACTGCTGGTGCGTGGCAGCCGTCTGTATCCGGATATTTTTCTGTTTCTGGGCTTTTG
CAACGAATTTCATGCCTATGGCTACGATTTTGAATATATTGCCCAGAAATGGAAAAGCAAAAAATACA
TTGGCTACTGGCAGAGCGAACACTTTTTTCATAAACATATTCTGGACCTGAAAGAATTTTTTATTCCG
AAAAATGTGAGCGAACAGGCAAATCTGCTGGCAGCAAAAATTCTGGAAAGCCAGAGCAGCCTGAGCAT
TCATATTCGTCGTGGCGATTATATTAAAAACAAAACCGCAACCCTGACACATGGTGTTTGTAGCCTGG
AATATTATAAAAAAGCCCTGAACAAAATCCGCGATCTGGCAATGATTCGTGATGTGTTTATCTTTAGC
GACGATATCTTCTGGTGCAAAGAAAATATTGAAACCCTGCTGAGCAAAAAATATAATATTTATTATAG
CGAAGATCTGAGCCAAGAAGAGGATCTGTGGCTGATGAGCCTGGCAAATCATCATATTATTGCCAATA
GCAGCTTTAGTTGGTGGGGTGCATATCTGGGTAGCAGCGCAAGCCAGATTGTTATTTATCCGACCCCG
TGGTATGATATTACCCCGAAAAACACCTATATCCCGATTGTGAACCATTGGATCAACGTTGATAAACA
TAGCAGCTGCTAA

Fig. 4D SEQ ID No. 4: <futC>

ATGGCCTTTAAAGTGGTTCAGATCTGCGGCGGTCTGGGCAATCAGATGTTTCAATATGCGTTCGCCAA
ATCACTGCAAAACATTCGAACACCCCGGTTCTGCTGGATATCACGAGTTTTGATTGGTCCGACCGTA
AAATGCAGCTGGAACTGTTCCCGATTGATCTGCCGTACGCAAGCGCTAAAGAAATCGCGATTGCCAAA
ATGCAGCACCTGCCGAAACTGGTCCGTGATGCACTGAAATGTATGGGCTTTGACCGCGTTTCACAAGA
AATTGTCTTCGAATATGAACCGAAACTGCTGAAACCGTCGCGTCTGACCTATTTCTTTGGTTACTTTC
AGGATCCGCGCTACTTCGACGCTATCTCTCCGCTGATTAAACAAACCTTTACGCTGCCGCCGCCGCCG

Fig. 4C (Continued)

```
GAAAACAACAAAAACAACAACAAAAAAGAAGAAGAATATCAGTGCAAACTGAGTCTGATCCTGGCGGC
CAAAAATTCCGTCTTTGTGCATATTCGTCGCGGCGATTACGTGGGCATCGGTTGTCAGCTGGGTATTG
ACTATCAGAAAAAAGCACTGGAATACATGGCTAAACGTGTGCCGAATATGGAACTGTTTGTTTTCTGC
GAAGATCTGGAATTTACCCAGAACCTGGACCTGGGCTATCCGTTCATGGATATGACCACGCGCGACAA
AGAAGAAGAAGCGTACTGGGATATGCTGCTGATGCAGTCATGTCAACATGGTATTATCGCCAATAGCA
CGTATTCTTGGTGGGCAGCTTACCTGATTGAAAACCCGGAAAAAATTATCATTGGCCCGAAACATTGG
CTGTTTGGTCACGAAAATATCCTGTGCAAAGAATGGGTCAAAATTGAAAGCCACTTCGAAGTGAAATC
TCAGAAATATAACGCGTAA
```

FERMENTATION PROCESS FOR PRODUCING MONOSACCHARIDES IN FREE FORM FROM NUCLEOTIDE-ACTIVATED SUGARS

CROSS-REFERENCE TO RELATED APPLICATIONS

This application is a National Stage entry of International Application No. PCT/EP2016/051919, filed Jan. 29, 2016, which claims priority to European Patent Application No. 15153383.3, filed Jan. 30, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence Listing 3000045-001000 ST25.txt" created on 18 Jul. 2017, and 19,754 bytes in size) is submitted concurrently with the instant application, and the entire contents of the Sequence Listing are incorporated herein by reference.

BACKGROUND

Field

The present invention relates to a microbial fermentation process for producing a monosaccharide of interest in free form from nucleotide-activated sugars.

Description of Related Art

Carbohydrates play roles in all forms of life by taking on vital roles in energy storage, structural function, signalling, information storage etc. For this task nature synthesizes several major monosaccharides like glucose, N-acetyl-glucosamine, mannose, N-acetyl-mannosamine, fructose, fucose, ribose, sialic acid, xylose etc. and several minor ones for more specialized applications, like for example D-allose.

L-fucose (6-deoxy-L-galactose) and fucosylated oligo-, and polysaccharides are of great interest for the chemical, cosmetic and pharmaceutical industry since they have high potential for nutritional and biomedical applications (Hauber, H.-P., Schulz, M., Pforte, A., Mack, P., Zabel, P. & Schumacher, U. (2008) Inhalation with fucose and galactose for treatment of *Pseudomonas aeroginosa* in cyctric fibrosis patients. *Int. J. Med. Sci.* 5, 371-376; Isnard, N., Bourles-Dagonet F., Robert, L. & Renard, G. (2005) Studies on corneal wound healing: Effects if fucose on iodine vapor-burnt rabbit corneas. *Ophthalmologica* 219, 324-333; Robert, L., Fodil-Bourahla, I., Bizbiz, L. & Robert, A. M. (2004) Effect of L-fucose and fucose-rich polysaccharides on elastin biosynthesis, in vivo and in vitro. *Biomed. Pharmacother.* 58, 123-128; Wild, M. K., Lühn, K., Marquardt, T. & Vestweber, D. (2002) Leukocyte adhesion deficiency II: therapy and genetic defect. *Cells Tissues Organs* 172, 161-173; Adam, E. C., Mitchell, B. S., Schumacher, D. U., Grant, G. & Schumacher, U. (1997) *Pseudomonas aeruginosa* II lectin stops human ciliary beating: therapeutic implications of fucose. *Am. J. Respir. Care Med.* 155, 2102-2104). They are known to have anti-inflammatory, anti-viral, and anti-tumor properties and also act as prebiotics. Due to the anti-aging effect L-fucose is also of interest for cosmetics (Isnard, N., Fodil-Bourathla, I., Robert A. M. & Robert, L. (2004) Pharmacology of skin aging. Stimulation of glycosaminoglycan biosynthesis by L-fucose and fucose rich polysaccharides, effect of in vitro aging of fibroblasts. *Biomed. Pharmacother.* 58, 202-204.). In addition fucosylated derivatives are known for their antiallergic and emulsifying properties.

Whereas some monosaccharides can be obtained from nature in large amounts and at reasonable cost (e.g. glucose, N-acetylglucosamine, and fructose), most monosaccharides are rather scarce and can be found in nature only in small amounts, like for example L-fucose (6-deoxy-L-galactose).

For commercial production of monosaccharides, almost exclusively oligosaccharides obtained from nature are used as sources. These oligosaccharides are acid hydrolyzed and from the released monosaccharides the individual sugars are purified. Due to the high chemical similarity of the monosaccharides (mostly differing from each other only by the orientation of individual hydroxyl-groups) the separation of individual monosaccharides in pure form is rather laborious and costly.

L-fucose represents such a rare sugar, which is currently obtained via the hydrolysis of complex oligosaccharides, either from algae or bacterial origin. For the purification of individual monosaccharides from complex hydrolysates often noxious chemical have to be employed, like for example lead acetate and excessive amounts of organic solvents (Schweiger, R. G. (1966) Preparation of α-L-fucosides and L-fucose from fucoidan. U.S. Pat. No. 3,240, 775). Therefore, the isolation of individual monosaccharides from a complex hydrolysate of oligosaccharides is challenging (due to the high chemical similarity of the individual monosaccharides released) and environmentally harmful (due to the excessive use of toxic chemicals, such a lead carbonate). Also the availability of oligosaccharides rich in a certain sugar can be rather restricted in nature and also highly variable due to seasonal changes. L-Fucose represents such a scare monosaccharide which is traditionally obtained by the acid hydrolysis of fucose-containing polysaccharides. Fucose is mainly derived from the polysaccharide fucoidan, a fucan monosulfate present in all common brown seaweeds comprising the families Fucaceae and Laminariaceae (Black, W. A. P (1954): The seasonal variation in the combined L-fucose content of the common british Laminariaceae and Fucaceae. *J. Sci. Food Agric.* 5, 445-448). Today, L-fucose is obtained in large quantities mainly by the collection of brown seaweed belonging to the family Fucaceae, which can be found world-wide but in high amounts at the European shores of the Atlantic Ocean. The large-scale harvest of brown seaweed from sea shores causes environmental concerns and is limited by environmental protection laws.

For example, JP 2000351790 discloses a method for extracting fucoidan and for obtaining and separating a fucose-containing oligosaccharide from the extracted fucoidan.

Besides the hydrolysis of fucoidan from brown-seaweed recently a patent publication showed that L-fucose can also be obtained via the hydrolysis of natural occurring L-fucose containing bacterial polysaccharides: WO 2012/034996 A 1 discloses a strain belonging to the Enterobacteriaceae family, which strain is able to produce extracellular polysaccharides which contain L-fucose. For the production of L-fucose, the polysaccharides produced by the strain are recovered and subjected to hydrolysis, e.g. by treatment with sulphuric acid or trifluoroacetic acid.

WO 2014067696 A1 describes for the first time a process for production of L-fucose by using a recombinant microorganism that possesses a glycosyltransferase and a glycosidase which work together to synthesize L-fucose in a free form. This process needs two enzymes and an acceptor molecule. The glycosyltransferase catalyses the transfer of fucose from GDP-L-fucose to the acceptor, for example lactulose, to synthesize fucosyllactulose. The Fucosylated acceptor (e.g. Fucosyllactulose) is then hydrolysed by a glycosidase into the acceptor molecule and L-fucose. The acceptor is then again available for fucosylation by the employed fucosyltransferase. L-fucose is then liberated from the cell by export into the medium were it can be retrieved from the supernatant. By this means the feedback inhibition of the GDP-fucose pathway can be easily overcome and significant (several g/l) amounts of free L-fucose can be obtained by microbial fermentation.

Besides the extraction of L-fucose from poly- or oligo-saccharide hydrolysates, several synthetic routes for L-fucose have been developed starting from other monosaccharides, like L-arabinose, D-galactose, L-rhamnose, D-mannose and D-glucose. With the most efficient synthetic route developed by Defraye et al (1984) starting from the rare monosaccharide L-rhamnose (Defaye, J., Gadelle, A. & Angyal, S. (1984) An efficient synthesis of L-fucose and L-(4-$^2$H)fucose. *Carbohydr. Res.* 126, 165-169). Generally the yields of these chemical syntheses are often rather poor and involve several chemical steps. Besides involving several synthetic steps, extensive protection group chemistry has to be used for the chemical synthesis of L-fucose. In general, the large-scale chemical synthesis of monosaccharides have not proved economical viable in comparison to extraction of L-fucose from polysaccharides collected from nature.

Thus, currently, the preparation of any monosaccharide in pure form requires a significant effort in the purification of other monosaccharides away from the target monosaccharide, often involving large volumes of organic solvents and other noxious chemicals. As a consequence, the exclusive accumulation of a single desired monosaccharide, like for example L-fucose, would be of immense help. However most microorganisms are restricted in the kinds of monosaccharides they are able to utilize. In addition, they often exert strong preferences towards certain monosaccharides in case that several monosaccharides are available at the same time as carbon source.

SUMMARY

In view of the above, it is an object of the present invention to provide a new process for the production of a single desired monosaccharide in free form, by means of which the monosaccharide can be retrieved fast and efficiently, i.e. in large scale and cost-effectively and without negative environmentally effects.

This and other objects are achieved by a process for producing, in large scale, a monosaccharide of interest in free form using a microorganism, the process comprising the steps of:

a.) providing a microorganism for the synthesis of the monosaccharide comprising an enzyme capable of catalyzing the hydrolysis of a nucleotide-activated monosaccharide to release the monosaccharide of interest from the nucleotide-activated monosaccharide, and b.) cultivating the microorganism in a medium suitable for growing the microorganism, wherein the microorganism is unable to metabolize the monosaccharide to a significant extent, so that the monosaccharide of interest is produced and accumulates during cultivation step in free form.

The object underlying the invention is completely solved in this way.

DETAILED DESCRIPTION OF A PREFERRED EMBODIMENT

Applicant's above process has not previously been described, utilizes a microorganism comprising and expressing an enzyme that hydrolyses a nucleotide-activated monosaccharide and accumulates the free monosaccharide. The enzyme possessing hydrolysing activity on nucleotide-activated sugars can be, e.g., a fucosyltransferase, preferably a variant of the alpha-1,2-fucosyltransferase encoded by the wbgL gene of *E. coli*:O126 (acc. No. ADN43847) or the 1,2-fucosyltransferase futC from *Helicobacter pylori* (acc. No. AAD29868). Although unmodified microorganisms having the above described enzymatically features can be employed within the present invention, according to one aspect of the invention, the microorganism is a recombinant microorganism, wherein the recombinant microorganism has been transformed to comprise and express at least one nucleic acid sequence not naturally occurring in the microorganism and encoding an enzyme capable of catalyzing the hydrolysis of a nucleotide-activated monosaccharide.

In contrast to prior processes, a single enzyme capable of catalyzing the hydrolysis of, i.e. hydrolyzing, nucleotide-activated sugars, i.e. monosaccharides, is used to release the monosaccharide, whereas previous processes known in the art, employ at least one enzyme transferring the monosaccharide from a donor substrate to an acceptor substrate with a subsequent step of releasing the monosaccharide from the acceptor by means of a glycosidase. This step is not necessary in the present invention thereby facilitating the process for producing a monosaccharide of interest. Accordingly, in the process according to the invention, an enzyme is used that is capable of catalyzing the hydrolysis of nucleotide-activated monosaccharides and releasing the monosaccharide in free form "in the absence of an acceptor". Also, according to the invention, the process according to the invention is run without the targeted use of a glycosidase capable for releasing the monosaccharide from an acceptor-substrate.

With the newly provided process and the newly provided microorganism—recombinant or not—, it is possible to produce a desired monosaccharide in a free form and in large amounts, without necessitating chemicals or elaborate process steps. The process according to the invention represents a microbial fermentation process, suitable for getting employed for industrial large scale production of rare or other monosaccharides, which can be readily retrieved from the medium the microorganism is cultivated in.

The expression "monosaccharide" as used herein and as generally understood in the field of the invention, refers to the most basic unit of carbohydrates. Monosaccharides are the simplest form of sugar and are usually colourless, water-soluble, crystalline solids. Examples of monosaccharides include glucose, fructose, galactose, xylose, mannose, fucose, rhamnose and ribose. Monosaccharides are the building blocks of disaccharides such as sucrose and polysaccharides such as cellulose and starch. "Oligosaccharide" as the term is used herein and as generally understood in the state of the art, refers to a saccharide polymer containing two monosaccharides or more.

The term "nucleic acid sequence encoding . . ." generally refers to any polyribonucleotide or polydeoxyribonucleotide, which may be unmodified RNA or DNA or modified RNA or DNA, and generally represents a gene which encodes a certain polypeptide or protein. The term includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. The term also encompasses polynucleotides that include a single continuous region or discontinuous regions encoding the polypeptide (for example, interrupted by integrated phage or an insertion sequence or editing) together with additional regions that also may contain coding and/or non-coding sequences.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

In the present invention the term "nucleotide-activated monosaccharide" used in combination with the "enzyme capable of catalyzing the hydrolysis of a nucleotide-activated monosaccharide", or "enzyme capable of hydrolysing a nucleotide-activated monosaccharide", describes an enzyme possessing catalytic activity on nucleotide-activated monosaccharides; hydrolysis leads to release of the desired monosaccharide. In this connection, the term "glycosyltransferase" designates and encompasses enzymes that catalyse the transfer of monosaccharide moieties from an activated nucleotide monosaccharide (the "glycosyl donor") to a glycosyl acceptor molecule. In the present invention, the glycosyltransferase used in the process and microorganism according to the invention does catalyze the hydrolysis of the nucleotide-activated monosaccharide in absence of the acceptor molecule. According to one aspect of the invention, it is particularly preferred if the nucleotide-activated sugar hydrolase is a bacterial fucosyltransferase, and preferably a variant of the alpha-1,2-fucosyltransferase encoded by the wbgL gene of *E. coli*:O126 (acc. No. ADN43847) or other fucosyltransferases catalysing hydrolysis of GDP-L-fucose in the absence of an acceptor molecule.

Accordingly, the term nucleotide-activated sugar hydrolase or a nucleic acid/polynucleotide encoding an nucleotide-activated sugar hydrolase refer to an enzyme that catalyses hydrolytic cleavage of nucleotide-activated sugars, such as GDP-fucose, UDP-galactose, GDP-mannose, GDP-rhamnose, and other nucleotide sugars naturally occurring. Preferably this nucleotide-activated sugar hydrolase is a glycosyltransferase that does not or predominantly not transfer the monosaccharide to an acceptor molecule. In the case of GDP-L-fucose, the enzyme capable of hydrolyzing a nucleotide-activated monosaccharide is a fucosyltransferase, e.g. but not limited to, a alpha-1,2-fucosyltransferase.

More specific, it is preferred if the alpha-1,2-fucosyltransferase WbgL from *E. coli*:126 possessing the amino acid residues substitutions asparagine 69 to serine, histidine 124 to alanine, glutamate 215 to glycine, and isoleucine 268 to proline, or the 1,2-fucosyltransferase FutC from *Helicobacter pylori* or other fucosyltransferases exhibiting hydrolytic activity on GDP-L-fucose in the absence of an acceptor molecule is used.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, or 300, or more amino acids, to the amino acid sequences of the alpha-1,2-fucosyltransferases encoded by the wbgL gene of *E. coli*:O126 (acc. No. ADN43847) or futC of *H. pylori* (acc. No. AAD29868).

Additionally, the polypeptide of the hydrolysing enzyme may be altered by additions or deletions of peptide sequences in order to modify its activity. For example, polypeptide sequences may be fused to the enzymes polypeptide in order to effectuate additional enzymatic activity.

In addition, genes encoding an enzyme capable of hydrolyzing a nucleotide-activated monosaccharide may be altered so that the gene products include proteins or polypeptides that represent functionally equivalent gene products. Such an equivalent hydrolase gene product may contain deletions, additions or substitutions of amino acid residues within the amino acid sequence encoded by the hydrolase gene sequence described above, but which results in a silent change, thus producing a functionally equivalent gene product coding for an enzyme capable of hydrolyzing a nucleotide-activated monosaccharide. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Within the context of this invention, "functionally equivalent", as used herein, refers to a polypeptide capable of exhibiting a substantially similar in vivo hydrolase activity on nucleotide-activated sugars as the endogenous hydrolase gene product encoded by the hydrolase gene sequence described above, as judged by any of a number of criteria, including but not limited to antigenicity, i.e., the ability to bind to an anti-nucleotide-activated sugar hydrolase antibody, immunogenicity, i.e., the ability to generate an antibody which is capable of binding a nucleotide-activated monosaccharide hydrolase-protein or polypeptide, as well as enzymatic activity. Accordingly, the present invention also comprises enzymes that are functionally equivalent to the ones specifically disclosed.

Also, one skilled in the art will readily derive from the present invention, that any modification to the disclosed enzymes can be used within the process and microorganism of the present invention, which modification is leading to an increased hydrolysing activity of the described enzymes herein. Thus, such modified enzymes displaying an increased hydrolysing activity compared to the unmodified form are comprised by the invention as well.

Included within the scope of the invention are nucleotide-activated sugar hydrolase proteins, polypeptides, and derivatives (including fragments) which are differentially modified during or after translation. Furthermore, non-classical amino acids or chemical amino acid analogs can be introduced as a substitution or addition into the enzymes polypeptide sequence.

According to a preferred embodiment of the process according to the invention, the enzyme is a variant of the 2-fucosyltransferase encoded by the wbgL gene, or a variant of the 1,2-fucosyltransferase encoded by the futC gene from *Helicobacter pylori*, the variant carrying at least one, preferably at least two, and more preferably more than two modifications as compared to the wild type 2-fucosyltransferase encoded by the wbgL gene or to the wild type 1,2-fucosyltransferase encoded by the futC gene, respectively, the modification leading to an increased hydrolizing activity of the enzyme.

The enzyme capable of hydrolyzing nucleotide-activated sugars may be produced by recombinant DNA technology using techniques well known in the art. Methods which are well known to those skilled in the art can be used to construct expression vectors containing enzyme coding sequences and appropriate transcriptional translational control signals that permit synthesis of an enzyme catalysing hydrolysis of nucleotide-activated sugars. These methods include, for example, in vitro recombinant DNA techniques, synthetic techniques, and in vivo genetic recombination. See, for example, the techniques described in Sambrook, J. and Russell D. W. (1989) Molecular Cloning: A Laboratory Manual, 2nd Ed., Cold Spring Harbor Laboratory Press, Cold Spring Harbor, N.Y.

According to an embodiment of the process according to the invention the at least one modification is at least one an amino acid substitution. According to another embodiment, the modification is or comprises at least one, two or more than two, in particular three, four, five, six, seven, eight, nine, or ten amino acids substitutions, wherein the modified enzyme capable of hydrolyzing a nucleotide-activated monosaccharide has an increased hydrolyzing activity on the nucleotide-activated monosaccharide compared to the unmodified wild-type enzyme.

According to one embodiment, it is preferred if the alpha-1,2-fucosyltransferase WbgL from *E. coli:*126 possessing the amino acid residues substitutions asparagine 69 to serine, histidine 124 to alanine, glutamate 215 to glycine, and isoleucine 268 to proline, or the 1,2-fucosyltransferase FutC from *Helicobacter pylori* or other fucosyltransferases exhibiting hydrolytic activity on GDP-L-fucose in the absence of an acceptor molecule is used.

One skilled in the art will appreciate from the disclosure of this invention, that not only the specific substitutions as specified above, but also other modifications of these specifically described enzymes, in particular other substitutions are encompassed by this invention, as long as the accordingly modified enzyme has an increased hydrolyzing activity on the nucleotide-activated monosaccharide compared to the unmodified wild-type enzyme. Alternative substitutions, which can be suitable, are also discussed above more generally, but should be applied here also.

Presently, and throughout the invention, "recombinant" means genetically engineered DNA prepared by transplanting or splicing genes from one species into the cells of a host microorganism of a different species. Such DNA becomes part of the host's genetic makeup and is replicated.

"Microorganism" presently designates and encompasses any microscopic organism that comprises either a single cell, cell clusters, or multicellular relatively complex organisms, which is suitable to be employed in the process according to the invention, and particularly includes bacteria and yeast. A microorganism as employed according to the invention can be cultivated in a liquid medium, and generally needs a carbon source in the medium to grow and replicate.

Consequently, "a recombinant host microorganism" is designated to mean any microorganism containing, a nucleic acid sequences coding for a glycosyltransferase or nucleotide-activated sugar hydrolase, or coding for a fucosyltransferase or a GDP-L-fucose hydrolase, wherein the nucleic acid sequences coding for these enzymes are nucleic acid sequences foreign to/not naturally occurring in the recombinant (host) cell and wherein the foreign/not naturally in said microorganism occurring sequence is integrated in the genome of the host microorganism cell. Thereby, "not naturally occurring" means that the nucleic acid sequence is foreign to said host microorganism cell, i.e. the nucleic acid sequences are heterologous with respect to the microorganism host cell. The heterologous sequence may be stably introduced, e.g. by transfection, transformation, or transduction, into the genome of the host microorganism cell, wherein techniques may be applied which will depend on the host cell the sequence is to be introduced. Various techniques are known to a person skilled in the art and are, e.g., disclosed in Sambrook et al., 1989, supra. Thus, the host cell the heterologous sequence has been introduced in, will produce the heterologous proteins the nucleic acid sequences according to the invention are coding for.

For recombinant production, host cells can be genetically engineered to incorporate expression systems or portions thereof and the nucleic acid sequences of the invention. Introduction of a nucleic acid sequence into the host microorganism cell can be effected by methods described in many standard laboratory manuals, such as Davis et al., Basic Methods in Molecular Biology, (1986), and Sambrook et al., 1989, supra.

Thus, the nucleic acid sequences according to the invention, may, e.g., be comprised in a vector which is to be stably transformed/transfected into host microorganism cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesise a polypeptide in a host may be used for expression in this regard. The appropriate DNA sequence may be inserted into the expression system by any of a variety of well-known and routine techniques, such as, for example, those set forth in Sambrook et al., supra.

As used herein, the term "recovering" means isolating, harvesting, collecting or otherwise separating from the microorganism culture the monosaccharide produced by the microorganism according to the invention.

According to a preferred embodiment of the process according to the invention, the microorganism is further modified to have inactivated or severely reduced or to lack catabolic pathways leading to the degradation of the produced monosaccharide.

According to yet another embodiment, the microorganism is further modified to have inactivated or severely reduced or to lack genes involved in the catabolism of L-fucose.

According to another embodiment, the microorganism is further modified to overexpress at least one gene involved in the biosynthesis of the nucleotide-activated monosaccharide to improve supply of the nucleotide-activated monosaccharide of the monosaccharide. In this regard it is preferred if the at least one gene is heterologous or homologous.

According to another embodiment of the process according to the present invention, at least one gene involved in the biosynthesis of GDP-fucose, GDP-mannose or GDP-rhamnose is overexpressed to improve supply of GDP-fucose, GDP-mannose or GDP-rhamnose, respectively. In this regard it is preferred if the at least one gene is heterologous or homologous.

According to another embodiment of the process according to the present invention, the microorganism is further modified to have inactivated or reduced competing pathways for the nucleotide-activated monosaccharide.

According to another embodiment of the process according to the present invention, the microorganism is further modified to express a phosphatase, in case where the monosaccharide is released in a phosphorylated form by the enzyme.

Throughout the invention, it is particularly preferred if the free monosaccharide to be produced is selected from L-fucose, L-rhamnose or L-mannose.

In a preferred embodiment, the microorganism is cultivated in a medium containing a carbon source that is selected from glycerol, sucrose, acetate, glucose, fructose, molasses, lactose, xylose, cellulose, syngas, carbon dioxide or carbon monoxide. In this context it is to be understood that any other—preferably low-cost—fermentation substrates can be employed as carbon source, and the person skilled in the art will readily able to employ a carbon source suitable within the present invention in order to grow the microorganism to produce the desired monosaccharide in large-scale.

According to one aspect of the invention, a carbon source is constantly added to the medium during the cultivating step of the microorganism, e.g. a recombinant microorganism.

By constantly adding the carbon source during the cultivation step, a constant and effective production of the monosaccharide is accomplished.

According to another aspect of the invention, the monosaccharide is recovered from supernatant of the cultivated recombinant host microorganism, which supernatant is obtained by centrifuging the cultivated host microorganism to obtain a supernatant and a host microorganism pellet.

With the newly provided process, it is possible to retrieve the produced monosaccharide from the medium the host microorganism is cultivated in, since the monosaccharide which is produced in a microorganism cell is transported into the medium, thus making it effortlessly possible to recover the monosaccharide from the supernatant, once the cells of the microorganism have been separated from the cultivation medium.

Other mono-, or oligosaccharides which may be produced in the microorganism during the synthesis of the desired the monosaccharide, and which mono-, or oligosaccharides impair/interfere with the recovering/purification step of the desired monosaccharide, can be metabolised by the microorganism, so that the recovering step of the desired monosaccharide is further improved and facilitated. Therefore saccharide metabolising enzyme(s)) may be externally added/supplied to the medium at the end of the process according to the invention. In doing so, undesired sugars cannot accumulate and do not interfere with the recovering of the desired monosaccharide. Genes encoding metabolic pathways or enzymes can be expressed in the microorganism in order to metabolize otherwise interfering undesired monosaccharides, and one skilled in the art will—upon reading the invention—readily recognize other suitable pathways or enzymes to deregulate/activate or supply, which will depend from the monosaccharide to be produced.

According to another aspect of the invention, the process according to the invention comprises the following steps:

a) providing, in a medium suitable for growing a microorganism, a recombinant host microorganism which has been transformed to comprise a nucleic acid sequence encoding an enzyme catalysing hydrolysis of nucleotide-activated monosaccharide not naturally occurring in the microorganism wherein the microorganism is unable to metabolize the monosaccharide to be produced in significant amounts, b) cultivating the recombinant host microorganism in said medium whereby the monosaccharide is produced in a free form, c) recovering the free monosaccharide from the medium.

Thus, the process as described in the above paragraphs comprises the additional step of recovering the free monosaccharide from the medium.

According to another aspect of the invention, there is disclosed and claimed a microorganism The definitions used and set forth above for specific terms in connection with the process do also apply for the recombinant microorganism presented therein.

According to a preferred embodiment, the microorganism—used in the process according to the invention and claimed therein—is selected from a bacterial or yeast strain able synthesize nucleotide-activated sugars from which the desired monosaccharide can be obtained by hydrolytic cleavage of the nucleotide-activated monosaccharide. The bacterium *Escherichia coli, Corynebacterium glutamicum* and the yeast Saccharomyces sp. have the advantage that these microorganisms can be grown easily and inexpensively in laboratory settings, and the bacterium and yeast have been intensively investigated for over many years.

Accordingly, in a preferred embodiment, the host microorganism used in the process according to the invention and otherwise claimed therein is selected from the group consisting of bacteria and yeast, and is preferably an *Escherichia coli* strain.

It is further preferred in an embodiment of the present invention, if the recombinant host microorganism is further modified to lack genes coding for enzymes involved in the metabolism of the desired monosaccharide, in the case of L-fucose as desired monosaccharide genes encoding L-fuculosose kinase, L-fucose isomerase, fuculose-1-phosphate aldolase, and UDP-glucose:undecaprenyl-phosphate glucose phosphotransferase. In addition, and according to a preferred embodiment, glycosyltransferase genes using the nucleotide-activated monosaccharide as substrate for the synthesis of polysaccharides (e.g. fucosyltransferases, or enzymes involved in the synthesis of fucosylated oligosaccharides such as colonic acid) are deleted.

Additionally, overexpression of genes improving synthesis of nucleotide-activated sugars is preferred. In the case of GDP-L-fucose genes encoding phosphomannomutase (manB), mannose-1-phosphate guanosyltransferase (manC), GDP-mannose-4,6-dehydratase (gmd), and GDP-L-fucose synthase (wcaG) from *E. coli* or adequate genes from other organisms are overexpressed in the respective microorganism.

This embodiment has the advantage that intracellular degradation of the produced monosaccharide L-fucose and production of colonic acid is prevented and synthesis of GDP-L-fucose is improved.

In another preferred embodiment, the recombinant host microorganism is further transformed to contain genes enabling the recombinant host microorganism to grow on sucrose or glycerol as sole carbon source, and it is particularly preferred if the csc-gene cluster of *Escherichia coli* W (acc. No. CP0021851) is integrated into the genome of the host microorganism, which gene cluster comprises the genes sucrose permase, fructokinase, sucrose hydrolase, and a transcriptional repressor (genes cscB, cscK, cscA, and cscR, respectively), that enable the transformed microorganism to grow on sucrose as sole carbon source.

In this connection it is noted that the embodiments listed as preferred for the process according to the invention all do apply for the claimed microorganism, where applicable.

Accordingly, the present invention also relates to the use of a microorganism possessing an enzyme catalysing the hydrolysis of nucleotide-activated monosaccharide wherein the microorganism is unable to metabolize the monosaccharide, and the invention further relates to the use of the recombinant microorganism according to the invention for the production of a monosaccharide, in particular of L-fucose.

It is noted that the definitions set forth above for describing certain terms of the process according to the invention shall apply for the microorganism, recombinant or unmodified, as claimed and described herein.

Alternatively, the method for producing monosaccharides may be applied on cell-free systems, whereby the enzyme according to the invention and suitable substrates are mixed in an aqueous reaction medium. The enzyme can be utilized free in solution, or they can be bound or immobilized to a support such as a polymer and the substrate may be added to the support. The support may be, e.g., packed in a column.

In particular, the present invention relates to a process wherein a recombinant *Escherichia coli* strain is used as recombinant host microorganism, wherein in the recombinant *Escherichia coli* strain the L-fucose isomerase gene, the L-fuculose kinase gene, and the UDP-glucose:undecaprenyl-phosphate glucose phosphotransferase have been deleted, and wherein the recombinant *Escherichia coli* strain has been transformed to comprise a) genes enabling the *E. coli* strain to grow on sucrose or glycerol as sole carbon source, the genes encoding, respectively, sucrose permase, fructokinase, sucrose hydrolase, and a transcriptional repressor, b) genes encoding phosphomannomutase, mannose-1-phosphate guanosyltransferase, GDP-mannose-4,6-dehydratase, and GDP-L-fucose synthase from *E. coli* or other organisms, c) a gene encoding an enzyme catalysing hydrolysis of nucleotide-activated monosaccharides, e.g. a fucosyltransferase that hydrolyses GDP-L-fucose in absence of an acceptor molecule. Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention. Also, it is noted that the particular features presented in the dependent claims can be combined with each other in other manners within the scope of the invention such that the invention should be recognized as also specifically directed to other embodiments having any other possible combination of the features of the dependent claims.

Figure 2:
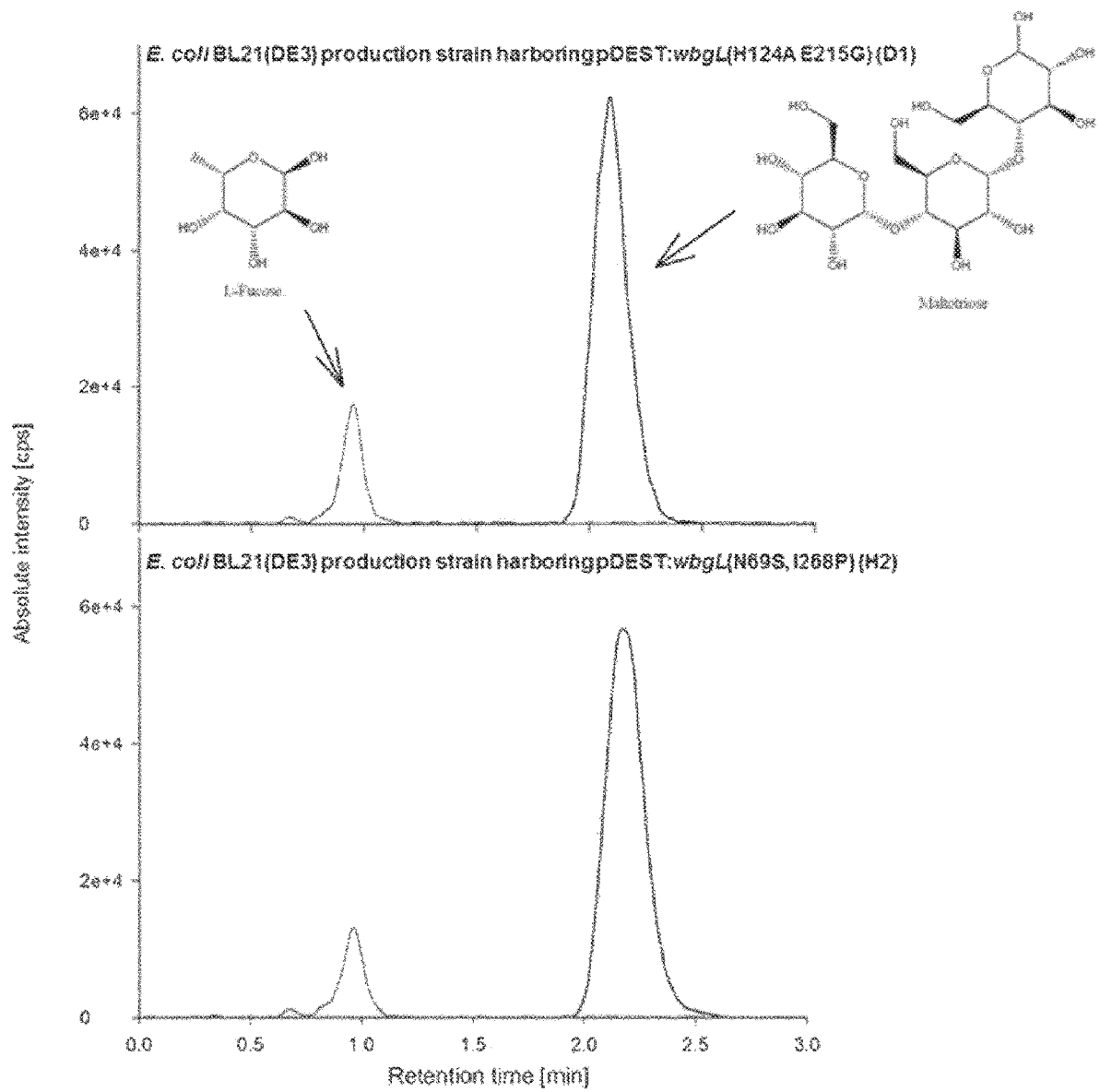
Figure 3:
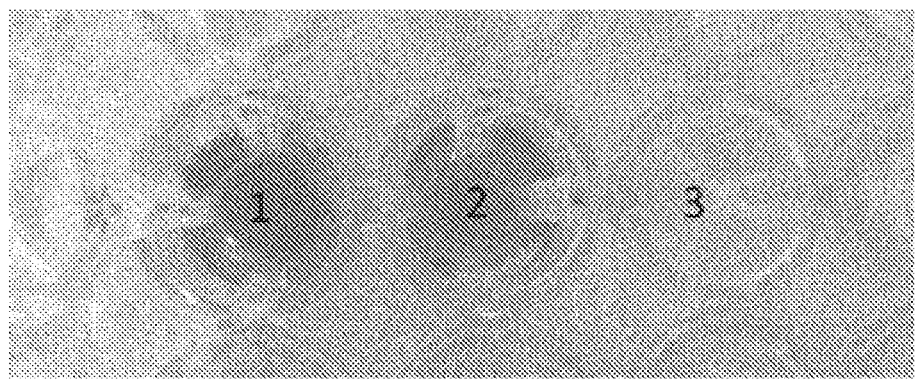

Several embodiments of the invention are illustrated in the figures and explained in more detail in the following description. In the figures:

FIG. 1 Detection of free L-fucose in the culture supernatant of an *E. coli* BL21(DE3) production strain containing a pDEST:wbgL library after random mutagenesis of wbgL by error-prone PCR. Supernatants of cultures from *E. coli* BL21(DE3) production strain harboring pDEST:wbgL(error-prone) clones were applied to a colorimetric L-fucose dehydrogenase assay. Well depicted as "WT" contained supernatant of an *E. coli* BL21(DE3) production strain pDEST:wbgL culture, expressing the unmodified wbgL gene. Wells signed "D1" and "H2" contained culture supernatant from clones synthesizing WbgL variants (H124A E215G) (clone D1) and WbgL (N69S I268P) (clone H2);

FIG. 2 LC-MS/MS analytics of culture supernatants of *E. coli* BL21(DE3) production strain harboring pDEST:wbgL (H124A E215G) (clone D1), and pDEST:wbgL(N69S I268P) (clone H2). 4.3 g/L, and 2.5 g/L L-fucose were produced by clones D1, and clone H2, respectively;

FIG. 3 Detection of L-fucose released from GDP-L-fucose by GDP-L-fucose hydrolase activity. Cell lysates of *E. coli* BL21(DE3) pDEST:futC and *E. coli* BL21(DE3) pDEST:wbgL (H124A E215G) were applied to an in vitro GDP-L-fucose hydrolase assays containing 5 mM GDP-L-fucose. Free L-fucose was detected in a colorimetric L-fucose dehydrogenase assay (for description of the assay see paragraph [0089] below). The assay in well 1 contained 0.27 units FutC, in well 2 0.32 units WbgL (H124A E215G) were applied. To confirm stability of GDP-L-fucose the assay was performed with bovine serum albumin (well 3); and FIG. 4 the sequence of <P1e1-manCB-PT5-gmd>(SEQ ID No: 1), wcaG- dhfr (A), <cscB-cscK-cscA-cscR>(SEQ ID No. 2) (B), <wbgL>(SEQ ID No. 3) (C), and <futC> (SEQ ID No. 4).

EXAMPLES

Construction of a Fucose Producing *E. coli* Strain

*Escherichia coli* BL21 (DE3) (Novagen, Darmstadt, Germany) was used for genetic manipulations to construct the fucose production strain. Since fucose is produced by hydrolysis of GDP-L-fucose, synthesis of GDP-L-fucose is enhanced by genomic integration and overexpression of the genes encoding phosphomannomutase (manB), mannose-1-phosphate guanosyltransferase (manC), GDP-mannose-4,6-dehydratase (gmd), and GDP-L-fucose synthase (wcaG) from *E. coli* K12 DH5α. The operon manC-manB is under transcriptional control of the $P_{tet}$ promotor and the operon gmd-wcaG is expressed from the $P_{T5}$ promotor. The gene cluster <$P_{tet}$-manCB-$P_{t5}$-gmd, wcaG-dhfr> (SEQ ID No. 1; FIG. 4A) comprises also the dhfr gene, encoding a dihydrofolate reductase that confers trimethoprim resistance to the integrants. For integration of the cluster into the *E. coli* BL21(DE3) genome by transposition, the cluster is flanked by inverted terminal repeats specifically recognized by the mariner-family transposable element Himar1. In addition the csc-gene cluster of *E. coli* W was introduced into the genome of the host organism. The gene cluster comprises the genes for sucrose permease (cscB), fructokinase (cscK), sucrose hydrolase (cscA), and a transcriptional repressor (cscR). Integration of the cluster <cscB-cscK-cscA-cscR> (SEQ ID No. 2; FIG. 4B) that was flanked by Himar1 specific inverted terminal repeats was performed by Himar1 transposition and mediates to the host organism the ability to grow on sucrose as sole carbon source (Choi, K.-H. and Kim, K.-J. (2009) Applications of transposon-based gene delivery system in bacteria. *J. Microbiol. Biotechnol.* 19, 217-228).

To prevent GDP-L-fucose depletion by formation of colonic acid the gene wcaJ predicted to encode a UDP-glucose:undecaprenyl phosphate glucose-1-phosphate transferase was deleted from the *E. coli* BL21(DE3) genome according to the method of Datsenko and Warner (Datsenko, K. A. and Warner B. L. (2000) One-step inactivation of chromosomal genes in *Escherichia coli* K-12 using PCR products. *Proc. Natl. Acad. Sci. USA* 97, 6640-6645). The UDP-glucose:undecaprenyl phosphate glucose-1-phosphate transferase catalyzes the first step in colonic acid synthesis (Stevenson, G., Andrianopoulos, K., Hobbs, M. and Reeves, P. R. (1996) Organization of the *Escherichia coli* K-12 gene cluster responsible for production of the extracellular polysaccharide colonic acid. *J. Bacteriol.* 178, 4885-4893). Additionally, the genes fucI and fucK of the fucose catabolic pathway, encoding the fucose isomerase and fuculose kinase, respectively, were inactivated by genomic knock-out to inhibit degradation of L-fucose.

Cloning of the 2-Fucosyltransferases Genes wbgL and futC, and Mutagenesis of wbgL The 2-fucosyltransferase gene wbgL (SEQ ID No. 3; FIG. 4C) from *E. coli*:O126 (acc. No. AND43847) was codon-optimized and prepared synthetically by GenScript Cooperation (Piscataway, USA). Also the futC (SEQ ID No. 4, FIG. 4D) gene encoding 1,2-fucosyltransferase from *Helicobacter pylori* (acc. No. AAD29868) was synthetically synthesized and codon optimized for expression in *E. coli*. For cloning into the vector pDEST14 the genes were amplified using primers 6128 (SEQ ID No. 5) and 6129 (SEQ ID No. 6) for wbgL, and primers 6195 (SEQ ID No. 7) and 6196 (SEQ ID No. 8) for futC, respectively; for primer sequences see table 1 below:

TABLE 1

List of oligonucleotides used for polymerase chain reaction

| primer | Sequence 5'-3' |
| --- | --- |
| 6128 | GGGGACAAGTTTGTACAAAAAAGCAGGCTTCGAAGGAGATACAACATGGGCAGCATTATTCGTCTGCAGGGTGG (SEQ ID No. 5) |
| 6129 | GGGGACCACTTTGTACAAGAAAGCTGGGTTTAGCAGCTGCTATGTTTATCAACGTTGATC (SEQ ID No. 6) |
| 6195 | GGGGACAAGTTTGTACAAAAAAGCAGGCTTCGAAGGAGGTAGAACATGGCCTTTAAAGTGGTTCAGATCTGCGGC (SEQ ID No. 7) |
| 6196 | GGGGACCACTTTGTACAAGAAAGCTGGGTCCTATTACGCGTTATATTTCTGAGATTTCACTTCG (SEQ ID No. 8) |

Mutations in the wbgL gene were introduced by several rounds of error-prone PCR using the Diversify® PCR Random Mutagenesis Kit (Clonetech, Mountain View, USA) according to the manufactures instructions and primers 6128 and 6129. Purified error-prone PCR products were cloned into vector pDEST14 yielding pDEST:wbgL(error-prone). Cloning into vector pDEST14 was generally performed using the Gateway technology (Gateway® Technology manual (Life Technologies, Carlsbad, USA)). Sequencing of the plasmids was performed by LGC Genomics (Berlin, Germany). Recombinant plasmids were transformed in suitable *E. coli* hosts by electroporation.

Growth Media and Cell Cultivation

The *E. coli* BL21(DE3) production strain harboring the pDEST:wbgL(error-prone) plasmid library was grown in mineral salts medium with 1% (v/v) glycerol and 1% (v/v) sucrose as carbon sources. The medium consists of 2 g/L $NH_4H_2PO_4$, 7 g/L $K_2HPO_4$, 2 g/L KOH, 0.3 g/L citric acid, 0.98 g/L $MgSO_4 \times 7$ $H_2O$, and 0.02 g/L $CaCl_2 \times 6$ $H_2O$. It is supplemented with one milliliter per liter trace element solution (54.4 g/L ammonium ferric citrate, 9.8 g/L $MnCl_2 \times 4$ $H_2O$, 1.6 g/L $CoCl_2 \times 6$ $H_2O$, 1 g/L $CuCl_2 \times 2$ $H_2O$, 1.9 g/L $H_3BO_3$, 9 g/L $ZnSO_4 \times 7$ $H_2O$, 1.1 g/L $Na_2MoO_4 \times 2$ $H_2O$, 1.5 g/L $Na_2SeO_3$, 1.5 g/L $NiSO_4 \times 6$ $H_2O$). For selection 10 µg/mL trimethoprim and 100 µg/mL ampicillin were added. Cells were grown in 96-well microtiter plates for 24 hours at 30° C. with shaking. 50 µl of the preparatory cultures were transferred to 96-well plates with 400 µl fresh HEPES (100 mM) buffered medium containing 0.3 mM IPTG to induce expression of wbgL genes in pDEST. Induced cultures were grown for two days at 30° C. with shaking. Cells were sedimented by centrifugation and the supernatant was used for detection of free L-fucose.

*E. coli* BL21(DE3) containing pDEST: wbgL (H124A E215G) and pDEST:futC, respectively, was grown in 2YT broth (Sambrook, J. and Russell D. W. (1989) Molecular Cloning: A Laboratory Manual, 2nd Ed., Cold Spring Harbor Laboratory Press, Cold Spring Harbor, N.Y.) at 30° C. to an OD600 nm of 0.3 in the presence of 100 µg/mL ampicillin. Transcription of wbgL (H124A E215G) and futC was induced by addition of 0.3 mM IPTG. Cells were harvested by centrifugation 20h after induction. Cells were used for analysis of in vitro GDP-L-fucose hydrolase activity.

Enzyme Assays to Detect Free L-Fucose and In Vitro GDP-L-Fucose Hydrolase Activity Free L-fucose was measured in a colorimetric assay using L-fucose dehydrogenase (FuDH) from *Pseudomonas* sp. No. 1143 (acc. no. D32042) that catalyzes the NADP-dependent transformation of L-fucose to L-fucono-1,5-lactone. In the colorimetric assay nitroblue tetrazolium in the presence of phenazine methosulfate is reduced to a blue-purple formazan by NADPH. Formation of the formazan is monitored at 571 nm. (Mayer, K. M. and Arnold, F. H. (2002) A Colorimetric Assay to Quantify Dehydrogenase Activity in Crude Cell Lysates. *J. Biomol. Screen.* 7, 135-140).

The fuDH gene from *Pseudomonas* sp. No. 1143 was overexpressed in *E. coli* BL21(DE3). The recombinant FuDH protein that contained an N-terminal His6-tag was enriched from crude extract by immobilized-metal affinity chromatography using a Ni Sepharose™ 6 Fast Flow column (GE Healthcare, Pollards Wood, UK).

To detect free L-fucose in cultures of the fucose *E. coli* BL21(DE3) production strain harboring pDEST:wbgL(error-prone) each 200 µl L-fucose dehydrogenase assay reaction contained 50 µl cell culture supernatant and 150 µl of reagent solution that consists of 0.8 mM NADPH, 0.3 mM nitroblue tetrazolium, 0.03 mM phenazine methosulfate and 4.7 Units His6-FuDH in 50 mM Tris (pH 8.0) with 0.13% (w/v) gelatin (all chemicals were purchased from Sigma Aldrich, St. Louis, USA). Formation of the blue-purple formazan was measured after 10 min incubation at room temperature at 571 nm.

To detect GDP-L-fucose hydrolase activity in cell lysates of *E. coli* BL21(DE3) pDEST:wbgL (H124A E215G) and *E. coli* BL21(DE3) pDEST:futC cells were resuspended in 50 mM HEPES buffer (pH 7.5) with 5 mM $MnCl_2$ and disrupted using glasbeats and a Mini-Beatbeater (BioSpec Products, Bartlesville, USA). L-fucose was cleaved from GDP-L-fucose in a GDP-L-fucose hydrolase assay. 200 µl of the hydrolase assay contained 12.5 µl of 100 mM GDP-L-fucose (Sigma Aldrich, St. Louis, USA) in 50 mM HEPES buffer (pH 7.5), 5 mM $MnCl_2$ and 50 µl cell free extract.

To verify stability of GDP-L-fucose the hydrolase assay was also performed with 50 µl bovine serum albumin (30 mg/mL) instead of crude extract. Protein concentrations were estimated according to Bradford using a commercially available dye solution (Roti-Quant®, Carl Roth, Karlsruhe, Germany). After one hour incubation at 30° C. the enzymes in the GDP-L-fucose assays were inactivated by heating to 95° C. for 10 min. 50 µl of the GDP-L-fucose hydrolase assay reaction mixture were used to detect free L-fucose using the L-fucose dehydrogenase assay. This assay was set up as described above and incubated for 24 h at room temperature.

LC-MS/MS Analysis

Mass spectrometry analysis was performed by MRM (multiple reaction monitoring) using a LC Triple-Quadrupole MS detection system (Shimadzu LC-MS 8050) (Shimadzu Corporation, Kyoto, Japan). Precursor ions are selected and analyzed in quadrupole 1, fragmentation takes place in the collision cell using argon as CID gas, selection of fragment ions is performed in quadrupole 3.

Chromatographic separation of fucose and maltotriose after dilution of culture supernatant and reaction mixture from in vitro assay, respectively, 1:100 with 10 µg/mL maltotriose in $H_2O$ (LC/MS Grade), was performed on a XBridge Amide HPLC column (3.5 µm, 2.1×50 mm (Waters, USA) with a XBridge Amide guard cartridge (3.5 µm, 2.1×10 mm) (Waters, USA). The HPLC system consists of a Shimadzu Nexera X2 SIL-30$AC_{MP}$ Autosampler run at 8° C., a Shimadzu LC-20AD Pump, and a Shimadzu CTO-20AC column oven that was run at 30° C. (Shimadzu Corporation, Kyoto, Japan). The mobile phase was composed of acetonitrile:$H_2O$ (62:38% (v/v)) with 10 mM ammonium acetate. A 1 µl sample was injected into the instrument; the run was performed for 3 min with a flow rate of 300 µl/min. L-fucose and maltotriose (added as internal standard for normalization) were analyzed by MRM in ESI negative ionization mode. The mass spectrometer was operated at unit resolution. Fucose forms an ion of m/z 163.2 [M-H] and maltotriose an ion of m/z 503.2 [M-H]. The precursor ion of L-fucose was further fragmented in the collision cell into the fragment ions m/z 88.9, m/z 70.8 and m/z 58.9. The molecular ion of maltotriose (m/z 503.2) was fragmented into m/z 341.1, m/z 161.05 and m/z 100.9. Collision energy, Q1 and Q3 Pre Bias were optimized for each analyte individually.

Results

Synthesis of Free L-Fucose by the *E. coli* BL21(DE3) Production Strain Expressing a Fucosyltransferase Gene To enhance GDP-L-fucose synthesis in *E. coli* BL21 (DE3) heterologous genes encoding phosphomannomutase, mannose-1-phosphate guanosyltransferase, GDP-mannose-4,6-dehydratase, and GDP-L-fucose synthase were genomically integrated and overexpressed. Additionally, to confer to the BL21(DE3) strain the ability to grow on sucrose, the csc-gene cluster, encoding sucrose permease, fructokinase, sucrose hydrolase and a transcriptional repressor, from *E. coli* W was integrated in the genome.

The 2-fucosyltransferase WbgL catalyzes the transfer of L-fucose from the donor molecule GDP-L-fucose to an acceptor oligosaccharide. However, in the absence of an acceptor molecule free L-fucose could be detected in the supernatant of the bacterial cultures, when growing the *E. coli* BL21(DE3) production strain harboring pDEST:wbgL in an appropriate medium. Free L-fucose is released from GDP-fucose by the GDP-L-fucose hydrolase activity of WbgL.

To further improve the GDP-L-fucose hydrolase activity of WbgL the wbgL gene was subjected to random mutagenesis using error-prone PCR. A library of about 5000 *E. coli* BL21(DE3) production strains harboring pDEST:wbgL(error-prone) clones was tested for improved GDP-L-fucose hydrolase activity. Two clones (designated as clones D1 and H2) showed increased production of free L-fucose, as determined by analysis of culture supernatants using the L-fucose dehydrogenase assay (FIG. 1). Two amino acid substitutions were found in the WbgL sequence of each of the two clones. The WbgL variant of clone D1 contained amino acid substitutions histidine 124 to alanine and glutamate 215 to glycine, in the WbgL variant of clone H2 residue asparagin 69 was exchanged to serine and isoleucine 268 to proline.

Supernatants of the *E. coli* BL21(DE3) production strain harboring plasmids pDEST:wbgL, pDEST:wbgL(H124A E215G) D1 and pDEST:wbgL(N69S I268P) H2 were also subjected to LC-MS/MS analysis. L-fucose was identified by MRM analysis in each sample. The amount of free L-fucose was determined using maltotriose as an internal standard for normalization. For the strain expressing the wbgL wild-type gene 0.12 g/L L-fucose were determined in the culture supernatant. Hydrolytic activity of WbgL variants (H124A, E215G), and (N69S, I268P) was clearly increased. Clones D1 and H2 produced 0.43 g/L and 0.25 g/L L-fucose, respectively (FIG. 2).

Detection of GDP-L-Fucose Hydrolase Activity in Cell Lysates of Microorganisms Expressing Fucosyltransferase Genes GDP-L-fucose hydrolase activity was analyzed in cell free extracts of *E. coli* BL21(DE3) pDEST:wbgL (H124A E215G) and *E. coli* BL21(DE3) pDEST:futC, grown in the presence of the transcriptional inducer IPTG. The 2-fucosyltransferase FutC is described to hydrolyze GDP-L-fucose in the absence of an oligosaccharide substrate (Stein, D. B., Lin Y.-N., Lin, C.-H. (2008) Characterization of *Helicobacter pylori* α1,2-fucosyltransferase for enzymatic synthesis of tumor-associated antigens. *Adv. Synth. Catal.* 350, 2313-2321). GDP-L-fucose was cleaved in the hydrolase assay that contained 5 mM GDP-L-fucose and cell lysates of the respective strains. Using the L-fucose dehydrogenase assay free L-fucose was detected. No free L-fucose was detected in the assay containing bovine serum albumin instead of crude extract, demonstrating stability of GDPL-fucose (FIG. 3).

For quantification of the L-fucose released by in vitro hydrolyses of GDPL-fucose the hydrolase assays were cleared by solid phase extraction using ion exchange cartridges (Strata ABW, Phenomenex, Aschaffenburg, Germany) and analyzed by LCMS/MS. In assays containing cell lysates of the futC, and wbgL(H124A E215G) expressing strains, 0.38 g/L and 0.32 g/L L-fucose, respectively, were measured after 1 hour incubation, corresponding to specific GDP-L-fucose hydrolase activities of 0.18 U/mg for FutC and 0.21 U/mg for WbgL (H124A E215G).

The invention claimed is:

1. A process for producing L-fucose in free form using a recombinant host microorganism, the process comprising:
    A) obtaining a microorganism comprising GDP-L-fucose, wherein the microorganism comprises a recombinant nucleic acid sequence encoding a 1,2-fucosyltransferase that catalyzes the hydrolysis of the GDP-L-fucose to release the L-fucose from the GDP-L-fucose to produce free L-fucose in the absence of an acceptor molecule, wherein the 1,2-fucosyltransferase is an alpha-1,2-fucosyltransferase encoded by a wbgL gene from *Escherichia coli* set forth in SEQ ID NO: 3 or a 1,2-fucosyltransferase encoded by a futC gene from *Helicobacter pylori* set forth in SEQ ID NO: 4, or a gene encoding a 1,2-fucosyltransferase having at least 90% amino acid identity to the 1,2-fucosyltransferase encoded by the wbgL gene set forth in SEQ ID NO: 3 or the futC gene set forth in SEQ ID NO: 4;
    B) cultivating the recombinant microorganism in a medium suitable for growing the microorganism, and
    C) recovering the free L-fucose from the medium, wherein the microorganism is unable to metabolize the free L-fucose, and wherein the microorganism is *Escherichia coli* or a *Saccharomyces* spp.

2. The process of claim 1, wherein the microorganism has inactivated, reduced expression, or lacks one or more genes encoding an enzyme that catabolizes L-fucose, and wherein the gene is a fucose isomerase (fukI) or a fuculose kinase (fucK).

3. The process of claim 1, wherein at least one gene involved in encoding a protein for the biosynthesis of GDP-L-fucose is overexpressed, wherein the gene is selected from the group consisting of a gene encoding a phosphomannomutase (manB), a mannose-1-phosphate guanosyltransferase (manC), a GDP-mannose-4,6-dehydratase (gmd), and a GDP-L-fucosesynthase (wcaG), and wherein the man B, manC, gmd, and wcaG genes are from *Escherichia coli*.

4. The process of claim 1, wherein the microorganism is further modified to have inactivated or reduced competing pathways for the GDP-L-fucose.

5. The process of claim 1, wherein the microorganism is cultivated in a medium containing a carbon source selected from the group consisting of glycerol, sucrose, glucose, fructose, molasse, xylose, cellulose, syngas, corn-syrup or lactose.

6. An *Escherichia coli* comprising a recombinant nucleic acid sequence encoding an enzyme that catalyzes the hydrolysis of GDP-L-fucose to release L-fucose from the GDP-L-fucose in the absence of an acceptor molecule, wherein the enzyme is a bacterial alpha-1,2-fucosyltransferase, wherein the bacterial alpha-1,2-fucosyltransferase is encoded by a wbgL gene from *Escherichia coli* set forth in SEQ ID NO: 3 or the futC gene from *H. pylori* set forth in SEQ ID NO: 4, or a gene encoding a 1,2-fucosyltransferase having at least 90% sequence identity to the 1,2-fucosyltransferase encoded by the wbgL gene set forth in SEQ ID NO: 3 or the futC genes set forth in SEQ ID NO: 4, and wherein the microorganism is unable to metabolize the released L-fucose because of a disruption in a fucose isomerase (fukI) gene or fuculose kinase (fucK) gene.

7. The *Escherichia coli* of claim 6, which further comprises recombinant genes encoding a phosphomannomutase (manB), a mannose-1-phosphate guanosyltransferase (manC), a GDP-mannose-4,6-dehydratase (gmd), and a GDP-L-fucose synthase (wcaG), wherein the manB, manC, gmd, and wcaG genes are from *Escherichia coli* and wherein the genes are overexpressed.

8. The process of claim 1, wherein the recombinant microorganism is *Escherichia coli*.

9. The process of claim 1, wherein the 1,2-fucosyltransferase is a variant 1,2-fucosyltransferase comprising at least one of an asparagine to serine modification at amino acid residue 69 in the amino acid sequence encoded by SEQ ID NO: 3; a histidine to alanine modification at amino acid residue 124 in the amino acid sequence encoded by SEQ ID NO: 3; a glutamate to glycine modification at amino acid residue 215 in the amino acid sequence encoded by SEQ ID NO: 3; or an isoleucine to proline modification at amino acid residue 268 in the amino acid sequence encoded by SEQ ID NO: 3.

10. The recombinant *Escherichia coli* of claim 6, wherein the fucosyltransferase is a variant 1,2-fucosyltransferase comprising at least one of an asparagine to serine modification at amino acid residue 69 in the amino acid sequence encoded by SEQ ID NO: 3; a histidine to alanine modification at amino acid residue 124 in the amino acid sequence encoded by SEQ ID NO: 3; a glutamate to glycine modification at amino acid residue 215 in the amino acid sequence encoded by SEQ ID NO: 3; or an isoleucine to proline modification at amino acid residue 268 in the amino acid sequence encoded by SEQ ID NO: 3.

11. A recombinant *Escherichia coli* comprising a gene of SEQ ID NO: 3 or SEQ ID NO: 4 encoding a 1,2-fucosyltransferase of, and further comprising overexpression of a gene encoding a phosphomannomutase (manB), a mannose-1-phosphate guanosyltransferase (manC), a GDP-mannose-4,6- dehydratase (gmd), and a GDP-L-fucose synthase (wcaG), and wherein the *Escherichia coli* is unable to metabolize L-fucose because of a disruption in a fucose isomerase (fukI) gene or fuculose kinase (fucK) gene.

12. The recombinant *Escherichia coli* of claim 11, wherein the fucosyltransferase is a variant 1,2-fucosyltransferase comprising at least one of an asparagine to serine modification at amino acid residue 69 in the amino acid sequence encoded by SEQ ID NO: 3; a histidine to alanine modification at amino acid residue 124 in the amino acid sequence encoded by SEQ ID NO: 3; a glutamate to glycine modification at amino acid residue 215 in the amino acid sequence encoded by SEQ ID NO: 3; or an isoleucine to proline modification at amino acid residue 268 in the amino acid sequence encoded by SEQ ID NO: 3.

* * * * *

SEQUENCE LISTING

<160> NUMBER OF SEQ ID NOS: 8

<210> SEQ ID NO 1
<211> LENGTH: 6741
<212> TYPE: DNA
<213> ORGANISM: Artificial Sequence
<220> FEATURE:
<223> OTHER INFORMATION: <Ptet-manCB-PT5-gmd, wcaG-dhfr>

<400> SEQUENCE: 1

| | | | | | |
|---|---|---|---|---|---|
| ggccagatga | ttaattccta | attttgttg | acactctatc | attgatagag | ttattttacc | 60 |
| actccctatc | agtgatagag | aaaagtgaaa | tgaatagttc | gacaaaaatc | tagaaataat | 120 |
| tttgttaac | tttaagaagg | agatatacaa | tttcgtcgac | acacaggaaa | catattaaaa | 180 |
| attaaaacct | gcaggagttt | gaaggagata | gaaccatggc | gcagtcgaaa | ctctatccag | 240 |
| ttgtgatggc | aggtggctcc | ggtagccgct | tatggccgct | tccccgcgta | ctttatccca | 300 |
| agcagttttt | atgcctgaaa | ggcgatctca | ccatgctgca | aaccaccatc | tgccgcctga | 360 |
| acggcgtgga | gtgcgaaagc | ccggtggtga | tttgcaatga | gcagcaccgc | tttattgtcg | 420 |
| cggaacagct | gcgtcaactg | aacaaactta | ccgagaacat | tattctcgaa | ccggcagggc | 480 |
| gaaacacggc | acctgccatt | gcgctggcgg | cgctggcggc | aaaacgtcat | agcccggaga | 540 |
| gcgacccgtt | aatgctggta | ttggcggcgg | atcatgtgat | tgccgatgaa | gacgcgttcc | 600 |
| gtgccgccgt | gcgtaatgcc | atgccatatg | ccgaagcggg | caagctggtg | accttcggca | 660 |
| ttgtgccgga | tctaccagaa | accgttatg | gctatattcg | tcgcggtgaa | gtgtctgcgg | 720 |
| gtgagcagga | tatggtggcc | tttgaagtgg | cgcagtttgt | cgaaaaaccg | aatctggaaa | 780 |
| ccgctcaggc | ctatgtggca | agcggcgaat | attactggaa | cagcggtatg | ttcctgttcc | 840 |
| gcgccggacg | ctatctcgaa | gaactgaaaa | aatatcgccc | ggatatcctc | gatgcctgtg | 900 |
| aaaaagcgat | gagcgccgtc | gatccggatc | tcaattttat | tcgcgtggat | gaagaagcgt | 960 |
| ttctcgcctg | cccggaagag | tcggtggatt | acgcggtcat | ggaacgtacg | gcagatgctg | 1020 |
| ttgtggtgcc | gatggatgcg | ggctggagcg | atgttggctc | ctggtcttca | ttatgggaga | 1080 |
| tcagcgccca | caccgccgag | ggcaacgttt | gccacggcga | tgtgattaat | cacaaaactg | 1140 |
| aaaacagcta | tgtgtatgct | gaatctggcc | tggtcaccac | cgtcggggtg | aaagatctgg | 1200 |
| tagtggtgca | gaccaaagat | gcggtgctga | ttgccgaccg | taacgcggta | caggatgtga | 1260 |
| aaaaagtggt | cgagcagatc | aaagccgatg | gtcgccatga | gcatcgggtg | catcgcgaag | 1320 |
| tgtatcgtcc | gtggggcaaa | tatgactcta | tcgacgcggg | cgaccgctac | caggtgaaac | 1380 |
| gcatcaccgt | gaaaccgggc | gagggcttgt | cggtacagat | gcaccatcac | gcgcgcgaac | 1440 |
| actgggtggt | tgtcgcggga | acggcaaaag | tcaccattga | tggtgatatc | aaactgcttg | 1500 |
| gtgaaaacga | gtccatttat | attccgctgg | ggcgacgca | ttgcctggaa | acccggggga | 1560 |
| aaattccgct | cgatttaatt | gaagtgcgct | ccggctctta | tctcgaagag | gatgatgtgg | 1620 |
| tgcgtttcgc | ggatcgctac | ggacgggtgt | aaacgtcgca | tcaggcaatg | aatgcgaaac | 1680 |
| cgcggtgtaa | ataacgacaa | aaataaaatt | ggccgcttcg | gtcagggcca | actattgcct | 1740 |
| gaaaaagggt | aacgtatatga | aaaaattaac | ctgctttaaa | gcctatgata | ttcgcgggaa | 1800 |
| attaggcgaa | gaactgaatg | aagatatcgc | ctggcgcatt | ggtcgcgcct | atggcgaatt | 1860 |
| tctcaaaccg | aaaaccattg | tgttaggcgg | tgatgtccgc | ctcaccagcg | aaaaccttaaa | 1920 |
| actggcgctg | gcgaaaggtt | tacaggatgc | gggcgttgac | gtgctggata | ttggtatgtc | 1980 |
| cggcaccgaa | gagatctatt | cgccacgtt | ccatctcggc | gtggatggcg | gcattgaagt | 2040 |

```
taccgccagc cataatccga tggattataa cggcatgaag ctggttcgcg agggggctcg    2100
cccgatcagc ggagataccg gactgcgcga cgtccagcgt ctggctgaag ccaacgactt    2160
tcctcccgtc gatgaaacca aacgcggtcg ctatcagcaa atcaacctgc gtgacgctta    2220
cgttgatcac ctgttcggtt atatcaatgt caaaaacctc acgccgctca agctggtgat    2280
caactccggg aacggcgcag cgggtccggt ggtggacgcc attgaagccc gctttaaagc    2340
cctcggcgcg cccgtggaat taatcaaagt gcacaacacg ccggacggca atttccccaa    2400
cggtattcct aacccactac tgccggaatg ccgcgacgac acccgcaatg cggtcatcaa    2460
acacggcgcg gatatgggca ttgcttttga tggcgatttt gaccgctgtt tcctgtttga    2520
cgaaaagggg cagtttattg agggctacta cattgtcggc ctgttggcag aagcattcct    2580
cgaaaaaaat cccggcgcga agatcatcca cgatccacgt ctctcctgga acaccgttga    2640
tgtggtgact gccgcaggtg gcacgccggt aatgtcgaaa accggacacg cctttattaa    2700
agaacgtatg cgcaaggaag acgccatcta tggtggcgaa atgagcgccc accattactt    2760
ccgtgatttc gcttactgcg acagcggcat gatcccgtgg ctgctggtcg ccgaactggt    2820
gtgcctgaaa gataaaacgc tgggcgaact ggtacgcgac cggatggcgg cgtttccggc    2880
aagcggtgag atcaacagca aactggcgca acccgttgag gcgattaacc gcgtggaaca    2940
gcattttagc cgtgaggcgc tggcggtgga tcgcaccgat ggcatcagca tgacctttgc    3000
cgactggcgc tttaacctgc gcacctccaa taccgaaccg gtggtgcgcc tgaatgtgga    3060
atcgcgcggt gatgtgccgc tgatggaagc gcgaacgcga actctgctga cgttgctgaa    3120
cgagtaaaaa cgcggccgcg atatcgttgt aaaacgacgg ccagtgcaag aatcataaaa    3180
aatttatttg ctttcaggaa aattttttctg tataatagat tcataaattt gagagaggag    3240
tttttgtgag cggataacaa ttccccatct tagtatatta gttaagtata aatacaccgc    3300
ggaggacgaa ggagatagaa ccatgtcaaa agtcgctctc atcaccggtg taaccggaca    3360
agacggttct tacctggcag agtttctgct ggaaaaaggt tacgaggtgc atggtattaa    3420
gcgtcgcgca tcgtcattca acaccgagcg cgtggatcac atttatcagg atccgcacac    3480
ctgcaacccg aaattccatc tgcattatgg cgacctgagt gataccctca acctgacgcg    3540
cattttgcgt gaagtacagc cggatgaagt gtacaacctg ggcgcaatga gccacgttgc    3600
ggtctctttt gagtcaccag aatataccgc tgacgtcgac gcgatgggta cgctgcgcct    3660
gctggaggcg atccgcttcc tcggtctgga aagaaaaact cgtttctatc aggcttccac    3720
ctctgaactg tatggtctgg tgcaggaaat tccgcagaaa gagaccacgc cgttctaccc    3780
gcgatctccg tatgcggtcg ccaaactgta cgcctactgg atcaccgtta actaccgtga    3840
atcctacggc atgtacgcct gtaacggaat tctcttcaac catgaatccc cgcgccgcgg    3900
cgaaaccttc gttacccgca aaatcacccg cgcaatcgcc aacatcgccc aggggctgga    3960
gtcgtgcctg tacctcggca atatggattc cctgcgtgac tggggccacg ccaaagacta    4020
cgtaaaaatg cagtggatga tgctgcagca ggaacagccg gaagatttcg ttatcgcgac    4080
cggcgttcag tactccgtgc gtcagttcgt ggaaatggcg gcagcacagc tgggcatcaa    4140
actgcgcttt gaaggcacgg gcgttgaaga aagggcatt tggtttccg tcaccggca    4200 tgacgcgccg ggcgttaaac cgggtgatgt gattatcgct gttgaccgc gttacttccg    4260 tccggctgaa gttgaaacgc tgctcggcga cccgaccaaa gcgcacgaaa aactgggctg    4320
gaaaccggaa atcaccctca gagagatggt gtctgaaatg gtggctaatg acctcgaagc    4380
```

```
ggcgaaaaaa cactctctgc tgaaatctca cggctacgac gtggcgatcg cgctggagtc    4440
ataagcatga gtaaacaacg agtttttatt gctggtcatc gcgggatggt cggttccgcc    4500
atcaggcggc agctcgaaca gcgcggtgat gtggaactgg tattacgcac ccgcgacgag    4560
ctgaacctgc tggacagccg cgccgtgcat gatttctttg ccagcgaacg tattgaccag    4620
gtctatctgg cggcggcgaa agtgggcggc attgttgcca caacaccta tccggcggat    4680
ttcatctacc agaacatgat gattgagagc aacatcattc acgccgcgca tcagaacgac    4740
gtgaacaaac tgctgtttct cggatcgtcc tgcatctacc cgaaactggc aaaacagccg    4800
atggcagaaa gcgagttgtt gcagggcacg ctggagccga ctaacgagcc ttatgctatt    4860
gccaaaatcg ccgggatcaa actgtgcgaa tcatacaacc gccagtacgg acgcgattac    4920
cgctcagtca tgccgaccaa cctgtacggg ccacacgaca acttccaccc gagtaattcg    4980
catgtgatcc cagcattgct gcgtcgcttc cacgaggcga cggcacagaa tgcgccggac    5040
gtggtggtat ggggcagcgg tacaccgatg cgcgaatttc tgcacgtcga tgatatggcg    5100
gcggcgagca ttcatgtcat ggagctggcg catgaagtct ggctggagaa cacccagccg    5160
atgttgtcgc acattaacgt cggcacgggc gttgactgca ctatccgcga gctggcgcaa    5220
accatcgcca aagtggtggg ttacaaaggc cgggtggttt tgatgccag caaaccggat    5280
ggcacgccgc gcaaactgct ggatgtgacg cgcctgcatc agcttggctg gtatcacgaa    5340
atctcactgg aagcggggct tgccagcact taccagtggt ccttgagaa tcaagaccgc    5400
tttcgggggg ggagctaacg cgccatttaa atcaacctca gcggtcatag ctgtttcctg    5460
tgactgagca ataactagca taaccccttg gggcctctaa acgggtcttg aggggttttt    5520
tgctgaaacc aatttgcctg gcggcagtag cgcggtggtc ccacctgacc ccatgccgaa    5580
ctcagaagtg aaacgccgta cgcccgatgg tagtgtgggg tctccccatg cgagagtagg    5640
gaactgccag gcatcaaata aaacgaaagg ctcagtcgaa agactgggcc tttcgggatc    5700
caggccggcc tgttaacgaa ttaatcttcc gcggcggtat cgataagctt gatatcgaat    5760
tccgaagttc ctattctcta gaaagtatag gaacttcagg tctgaagagg agtttacgtc    5820
cagccaagct agcttggctg caggtcgtcg aaattctacc gggtagggga ggcgcttttc    5880
ccaaggcagt ctggagcatg cgctttagca gccccgctgg gcacttggcg ctacacaagt    5940
ggcctctggc ctcgcacaca ttccacatcc accggtaggc gccaaccggc tccgttcttt    6000
ggtggcccct tcgcgccacc ttctactcct cccctagtca ggaagttccc ccccgccccg    6060
cagctcgcgt cgtgcaggac gtgacaaatg gaagtagcac gtctcactag tctcgtgcag    6120
atggacagca ccgctgagca atggaagcgg gtaggccttt ggggcagcgg ccaatagcag    6180
ctttgctcct tcgctttctg ggctcagagg ctgggaaggg gtgggtccgg gggcgggctc    6240
aggggcgggc tcagggcgg ggcgggcgcc cgaaggtcct ccggaggccc ggcattctgc    6300
acgcttcaaa agcgcacgtc tgccgcgctg ttctcctctt cctcatctcc gggcctttcg    6360
acctgcagcc tgttgacaat taatcatcgg catagtatat cggcatagta taatacgaca    6420
aggtgaggaa ctaaccatgg gtcaaagta gcgatgaagc caacgctccc gttgcagggc    6480
agtttgcgct tcccctgagt gccacctttg gcttagggga tcgcgtacgc aagaaatctg    6540
gtgccgcttg gcagggtcaa gtcgtcggtt ggtattgcac aaaactcact cctgaaggct    6600
atgcggtcga gtccgaatcc cacccaggct cagtgcaaat ttatcctgtg gctgcacttg    6660
aacgtgtggc ctaatgaggg gatcaattct ctagagctcg ctgatcagaa gttcctattc    6720
tctagaaagt ataggaactt c                                              6741
```

<210> SEQ ID NO 2
<211> LENGTH: 5160
<212> TYPE: DNA
<213> ORGANISM: Artificial Sequence
<220> FEATURE:
<223> OTHER INFORMATION: <cscB-cscK-cscA-cscR>

<400> SEQUENCE: 2

```
gcgactgtac cagaacatga atgaggcgtt tggattaggc gattattagc agggctaagc      60
atttttactat tattattttc cggttgaggg atatagagct atcgacaaca accggaaaaa     120
gtttacgtct atattgctga aggtacaggc gtttccataa ctatttgctc gcgtttttta     180
ctcaagaaga aaatgccaaa tagcaacatc aggcagacaa tacccgaaat tgcgaagaaa     240
actgtctggt agcctgcgtg gtcaaagagt atcccagtcg gcgttgaaag cagcacaatc     300
ccaagcgaac tggcaatttg aaaaccaatc agaaagatcg tcgacgacag gcgcttatca     360
aagtttgcca cgctgtattt gaagacggat atgcacaaaa gtggaacctc aatggcatgt     420
aacaacttca ctaatgaaat aatccagggg ttaacgaaca gcgcgcagga aaggatacgc     480
aacgccataa tcacaactcc gataagtaat gcattttttg gccctacccg attcacaaag     540
aaaggaataa tcgccatgca cagcgcttcg agtaccacct ggaatgagtt gagataacca     600
tacaggcgcg ttcctacatc gtgtgattcg aataaacctg aataaagac aggaaaagt      660
tgttgatcaa aaatgttata gaaagaccac gtccccacaa taaatatgac gaaaacccag     720
aagtttcgat ccttgaaaac tgcgataaaa tcctctttttt ttaccccctcc cgcatctgcc     780
gctacgcact ggtgatcctt atctttaaaa cgcatgttga tcatcataaa tacagcgcca     840
aatagcgaga ccaaccagaa gttgatatgg ggactgatac taaaaaatat gccggcaaag     900
aacgcgccaa tagcatagcc aaaagatccc caggcgcgcg ctgttccata ttcgaaatga     960
aaatttcgcg ccattttttc ggtgaagcta tcaagcaaac cgcatcccgc cagatacccc    1020
aagccaaaaa atagcgcccc cagaattaga cctacagaaa aattgctttg cagtaacggt    1080
tcataaacgt aaatcataaa cggtccggtc aagaccagga tgaaactcat acaccagatg    1140
agcggtttct tcagaccgag tttatcctga acgatgccgt agaacatcat aaatagaatg    1200
ctggtaaact ggttgaccga ataaagtgta cctaattccg tccctgtcaa ccctagatgt    1260
cctttcagcc aaatagcgta taacgaccac cacagcgacc aggaaataaa aaagagaaat    1320
gagtaactgg atgcaaaacg atagtacgca tttctgaatg gaatattcag tgccataatt    1380
acctgcctgt cgttaaaaaa ttcacgtcct atttagagat aagagcgact cgccgtttta    1440
cttctcacta ttccagttct tgtcgacatg gcagcgctgt cattgcccct ttcgccgtta    1500
ctgcaagcgc tccgcaacgt tgagcgagat cgataattcg tcgcatttct ctctcatctg    1560
tagataatcc cgtagaggac agacctgtga gtaacccggc aacgaacgca tctcccgccc    1620
ccgtgctatc gacacaattc acagacattc agcaaaatg gtgaacttgt cctcgataac    1680
agaccaccac ccccttctgca cctttagtca ccaacagcat ggcgatctca tactcttttg    1740
ccagggcgca tatatcctga tcgttctgtg ttttttccact gataagtcgc cattcttctt    1800
ccgagagctt gacgacatcc gccagttgta gcgcctgccg caaacacaag cggagcaaat    1860
gctcgtcttg ccatagatct tcacgaatat taggatcgaa gctgacaaaa cctccggcat    1920
gccggatcgc cgtcatcgca gtaaatgcgc tggtacgcga aggctcggca gacaacgcaa    1980
ttgaacagag atgtaaccat tcgccatgtc gccagcaggg caagtctgtc gtctctaaaa    2040
```

-continued

```
aaagatcggc actggggcgg accataaacg taaatgaacg ttccccttga tcgttcagat    2100
cgacaagcac cgtggatgtc cggtgccatt catcttgctt cagatacgtg atatcgactc    2160
cctcagttag cagcgttctt tgcattaacg caccaaaagg atcatccccc acccgaccta    2220
taaacccact tgttccgcct aatctggcga ttcccaccgc aacgttagct ggcgcgccgc    2280
caggacaagg cagtaggcgc ccgtctgatt ctggcaagag atctacgacc gcatcccta    2340 aaacccatac tttggctgac atttttttcc cttaaattca tctgagttac gcatagtgat    2400
aaacctcttt ttcgcaaaat cgtcatggat ttactaaaac atgcatattc gatcacaaaa    2460
cgtcatagtt aacgttaaca tttgtgatat tcatcgcatt tatgaaagta agggacttta    2520
tttttataaa agttaacgtt aacaattcac caaatttgct taaccaggat gattaaaatg    2580
acgcaatctc gattgcatgc ggcgcaaaac gccctagcaa acttcatga gcaccggggt    2640 aacactttct atccccattt tcacctcgcg cctcctgccg ggtggatgaa cgatccaaac    2700
ggcctgatct ggtttaacga tcgttatcac gcgttttatc aacatcatcc gatgagcgaa    2760
cactgggggc caatgcactg gggacatgcc accagcgacg atatgatcca ctggcagcat    2820
gagcctattg cgctagcgcc aggagacgat aatgacaaag acgggtgttt ttcaggtagt    2880
gctgtcgatg acaatggtgt cctctcactt atctcacccg acacgtctg gctcgatggt    2940 gcaggtaatg acgatgcaat tcgcgaagta caatgtctgg ctaccagtcg ggatggtatt    3000
catttcgaga acagggtgt gatcctcact ccaccagaag gaatcatgca cttccgcgat    3060
cctaaagtgt ggcgtgaagc cgacacatgg tggatggtag tcggggcgaa agatccaggc    3120
aacacggggc agatcctgct ttatcgcggc agttcgttgc gtgaatggac cttcgatcgc    3180
gtactggccc acgctgatgc gggtgaaagc tatatgtggg aatgtccgga cttttttcagc   3240 cttggcgatc agcattatct gatgttttcc ccgcagggaa tgaatgccga gggatacagt    3300
taccgaaatc gctttcaaag tggcgtaata cccggaatgt ggtcgccagg acgacttttt    3360
gcacaatccg ggcattttac tgaacttgat aacgggcatg acttttatgc accacaaagc    3420 ttttagcga aggatggtcg gcgtattgtt atcggctgga tggatatgtg gaatcgcca     3480 atgccctcaa aacgtgaagg atgggcaggc tgcatgacgc tggcgcgcga gctatcagag    3540
agcaatggca aacttctaca acgcccggta cacgaagctg agtcgttacg ccagcagcat    3600
caatctgtct ctcccccgcac aatcagcaat aaatatgttt tgcaggaaaa cgcgcaagca    3660
gttgagattc agttgcagtg ggcgctgaag aacagtgatg ccgaacatta cggattacag    3720
ctcggcactg gaatgcggct gtatattgat aaccaatctg agcgacttgt tttgtggcgg    3780
tattacccac acgagaattt agacggctac cgtagtattc ccctcccgca gcgtgacacg    3840
ctcgccctaa ggatatttat cgatacatca tccgtggaag tatttattaa cgacggggaa    3900
gcggtgatga gtagtcgaat ctatccgcag ccagaagaac gggaactgtc gctttatgcc    3960
tcccacggag tggctgtgct gcaacatgga gcactctggc tactgggtta acataatatc    4020
aggtggaaca acgatcaac agcgggcaag ggatccgcgt cactcttccc ccttcacgac    4080
cttcaataat atgcaatgca gcttcccgcc cgataatgtc atgtggaagc tgaattgtgg    4140 tcagcggcg taaaaacaga tgcccgacgc caaccagatt atcaaagccc attacggcga    4200
catcctgcgg gattcgtacc cccttcgcca gaagaacctg ataagccaca aaggctgcgc    4260
gatcgttacc acatatcaga acatcaaaat ctggtttgcc cggtttgaag tgggcattga    4320
gtaaacttgc gagatcggtg tagtgatcat cacctgttgc catgtgaaat tgtttcacct    4380
cagccagatc tcgtccagca tcacgccagg cctgctcaaa tccctgccga cgatacctg    4440
```

| | |
|---|---|
| ttgccaacgc actttccggt agccagaagc ataacggttg acgatagccc gccgcgagca | 4500 |
| aatgctgtgt tgattcatat tgtgcagtgt aatcatcagg gatataactg ggtaacgctg | 4560 |
| ggtcatccgc cacacagttc gccaatacaa tattttcacc atacagagac tcaggcagcg | 4620 |
| tgatatgtcg cagccccatt gtagtataga taatgccatc cggacggtgg gcaagcagct | 4680 |
| gacgtgccgc gcgggcagcg tcatcttcag aaaaaatatt gattaaaaaa ctattccagc | 4740 |
| cgaactcgct ggcggtttgc tcaatggcaa gcagaatatc aacagagaaa ggagtggtag | 4800 |
| ccgtgtcctg cgccagcacg gcgagagtcg acggcttacg tccttgagcg cgcatcttac | 4860 |
| gggcggaaag atcaggaaca taattcaggg tctggattgc ctgcaatacg cggtcacgcg | 4920 |
| tgcaggacg cacagattct gcattatgca tcacccggga gactgtcatc atcgacactc | 4980 |
| ccgccaggcg tgcgacatcc tttaatgaag ccatacccaa gccgtttgcc gtaaaacggg | 5040 |
| cactgtagca gaaacagacg tcactggcga gatccaacgc cctatcacct gacacagcaa | 5100 |
| tacaataaaa aataacaata attcccggac aattgtcccc aattccgcct ctgttctcgc | 5160 |

<210> SEQ ID NO 3
<211> LENGTH: 897
<212> TYPE: DNA
<213> ORGANISM: Artificial Sequence
<220> FEATURE:
<223> OTHER INFORMATION: wbgL gene codon optimized

<400> SEQUENCE: 3

| | |
|---|---|
| atgggcagca ttattcgtct gcagggtggt ctgggtaatc agctgtttca gtttagcttt | 60 |
| ggttatgccc tgagcaaaat taatggtaca ccgctgtatt tcgacattag ccattatgcc | 120 |
| gaaaacgatg atcatggtgg ttatcgtctg aataatctgc agattccgga agaatatctg | 180 |
| cagtattata ccccgaaaat taataatatt tataaactgc tggtgcgtgg cagccgtctg | 240 |
| tatccggata ttttttctgtt tctgggcttt tgcaacgaat tcatgccta tggctacgat | 300 |
| tttgaatata ttgcccagaa atggaaaagc aaaaaataca ttggctactg gcagagcgaa | 360 |
| cacttttttc ataaacatat tctggacctg aaagaatttt ttattccgaa aaatgtgagc | 420 |
| gaacaggcaa atctgctggc agcaaaaatt ctggaaagcc agagcagcct gagcattcat | 480 |
| attcgtcgtg gcgattatat taaaaacaaa accgcaaccc tgacacatgg tgtttgtagc | 540 |
| ctggaatatt ataaaaaagc cctgaacaaa tccgcgatc tggcaatgat tcgtgatgtg | 600 |
| tttatcttta gcgacgatat cttctggtgc aaagaaaata ttgaaaccct gctgagcaaa | 660 |
| aaatataata tttattatag cgaagatctg agccaagaag aggatctgtg gctgatgagc | 720 |
| ctggcaaatc atcatattat tgccaatagc agctttagtt ggtggggtgc atatctgggt | 780 |
| agcagcgcaa gccagattgt tatttatccg accccgtggt atgatattac cccgaaaaac | 840 |
| acctatatcc cgattgtgaa ccattggatc aacgttgata acatagcag ctgctaa | 897 |

<210> SEQ ID NO 4
<211> LENGTH: 903
<212> TYPE: DNA
<213> ORGANISM: Artificial Sequence
<220> FEATURE:
<223> OTHER INFORMATION: futC codon optimized

<400> SEQUENCE: 4

| | |
|---|---|
| atggcccttta aagtggttca gatctgcggc ggtctgggca tcagatgtt tcaatatgcg | 60 |
| ttcgccaaat cactgcaaaa acattcgaac accccggttc tgctggatat cacgagtttt | 120 |

```
gattggtccg accgtaaaat gcagctggaa ctgttcccga ttgatctgcc gtacgcaagc      180
gctaaagaaa tcgcgattgc caaaatgcag cacctgccga aactggtccg tgatgcactg      240
aaatgtatgg gctttgaccg cgtttcacaa gaaattgtct tcgaatatga accgaaactg      300
ctgaaaccgt cgcgtctgac ctatttcttt ggttactttc aggatccgcg ctacttcgac      360
gctatctctc cgctgattaa acaaaccttt acgctgccgc cgccgccgga aaacaacaaa      420
aacaacaaca aaaagaaga agaatatcag tgcaaactga gtctgatcct ggcggccaaa      480
aattccgtct ttgtgcatat cgtcgcggc gattacgtgg gcatcggttg tcagctgggt      540
attgactatc agaaaaaagc actggaatac atggctaaac gtgtgccgaa tatggaactg      600
tttgttttct gcgaagatct ggaatttacc cagaacctgg acctgggcta tccgttcatg      660
gatatgacca cgcgcgacaa agaagaagaa gcgtactggg atatgctgct gatgcagtca      720
tgtcaacatg gtattatcgc caatagcacg tattcttggt gggcagctta cctgattgaa      780
aacccggaaa aaattatcat tggcccgaaa cattggctgt ttggtcacga aaatatcctg      840
tgcaaagaat gggtcaaaat tgaaagccac ttcgaagtga atctcagaa atataacgcg      900 taa                                                                   903

<210> SEQ ID NO 5
<211> LENGTH: 74
<212> TYPE: DNA
<213> ORGANISM: Artificial Sequence
<220> FEATURE:
<223> OTHER INFORMATION: Primer 6128

<400> SEQUENCE: 5
ggggacaagt ttgtacaaaa aagcaggctt cgaaggagat acaacatggg cagcattatt       60
cgtctgcagg gtgg                                                        74

<210> SEQ ID NO 6
<211> LENGTH: 60
<212> TYPE: DNA
<213> ORGANISM: Artificial Sequence
<220> FEATURE:
<223> OTHER INFORMATION: Primer 6129

<400> SEQUENCE: 6
ggggaccact ttgtacaaga aagctgggtt tagcagctgc tatgtttatc aacgttgatc       60

<210> SEQ ID NO 7
<211> LENGTH: 75
<212> TYPE: DNA
<213> ORGANISM: Artificial Sequence
<220> FEATURE:
<223> OTHER INFORMATION: Primer 6195

<400> SEQUENCE: 7
ggggacaagt ttgtacaaaa aagcaggctt cgaaggaggt agaacatggc ctttaaagtg       60
gttcagatct gcggc                                                       75

<210> SEQ ID NO 8
<211> LENGTH: 64
<212> TYPE: DNA
<213> ORGANISM: Artificial Sequence
<220> FEATURE:
<223> OTHER INFORMATION: Primer 6196
```

```
<400> SEQUENCE: 8
ggggaccact ttgtacaaga aagctgggtc ctattacgcg ttatatttct gagatttcac    60
ttcg                                                                 64
```